(12) United States Patent
Oosake et al.

(10) Patent No.: US 11,759,092 B2
(45) Date of Patent: Sep. 19, 2023

(54) ENDOSCOPE SYSTEM, PROCESSOR DEVICE, AND METHOD OF OPERATING ENDOSCOPE SYSTEM

(71) Applicant: FUJIFILM Corporation, Tokyo (JP)

(72) Inventors: Masaaki Oosake, Kanagawa (JP); Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 925 days.

(21) Appl. No.: 16/557,552

(22) Filed: Aug. 30, 2019

(65) Prior Publication Data

US 2019/0380617 A1 Dec. 19, 2019

Related U.S. Application Data

(63) Continuation of application No. PCT/JP2018/006547, filed on Feb. 22, 2018.

(30) Foreign Application Priority Data

Mar. 3, 2017 (JP) .................. 2017-040344

(51) Int. Cl.
*G06K 9/46* (2006.01)
*A61B 5/06* (2006.01)
(Continued)

(52) U.S. Cl.
CPC .... *A61B 1/000094* (2022.02); *A61B 1/00006* (2013.01); *A61B 1/00055* (2013.01); (Continued)

(58) Field of Classification Search
CPC . A61B 5/065; A61B 1/00006; A61B 1/00055; A61B 1/0638; A61B 5/1032; G06V 10/40
See application file for complete search history.

(56) References Cited

U.S. PATENT DOCUMENTS 4,622,954 A * 11/1986 Arakawa .............. A61B 1/0051
600/153
2008/0242931 A1 10/2008 Nishino
(Continued)

FOREIGN PATENT DOCUMENTS

| CN | 102201109 A | 9/2011 |
| CN | 102753078 A | 10/2012 |

(Continued)

OTHER PUBLICATIONS

Morimoto Yoshinori Translation of JP-2016007355, Jun. 2014 (Year: 2014).*

(Continued)

*Primary Examiner* — Zaihan Jiang
(74) *Attorney, Agent, or Firm* — Birch, Stewart, Kolasch & Birch, LLP

(57) ABSTRACT

An endoscope system comprises an image acquisition unit, a discrimination processing unit, and a discrimination processing control unit. The image acquisition unit acquires an endoscope image obtained by imaging an observation target using an endoscope. The discrimination processing unit discriminates a portion having a specific feature in the observation target by performing discrimination processing, using an endoscope image. The discrimination processing control unit controls a start or an end of the discrimination processing on the basis of a change in operation of an endoscope or the endoscope image.

30 Claims, 13 Drawing Sheets

(51) Int. Cl.
  *A61B 5/103* (2006.01)
  *A61B 1/00* (2006.01)
  *A61B 1/06* (2006.01)
(52) U.S. Cl.
  CPC ...... *A61B 1/000096* (2022.02); *A61B 1/0638* (2013.01); *A61B 5/065* (2013.01); *A61B 5/1032* (2013.01)

(56) References Cited

U.S. PATENT DOCUMENTS

| | | | |
|---|---|---|---|
| 2009/0076368 A1 | 3/2009 | Balas | |
| 2011/0235888 A1 | 9/2011 | Takahashi | |
| 2012/0120216 A1 | 5/2012 | Morita | |
| 2012/0281078 A1 | 11/2012 | Kobayashi et al. | |
| 2013/0243282 A1 | 9/2013 | Sato et al. | |
| 2016/0089010 A1 | 3/2016 | Aoyama | |
| 2017/0046833 A1* | 2/2017 | Lurie | G06T 7/579 |
| 2017/0251901 A1 | 9/2017 | Miyai | |
| 2021/0401527 A1* | 12/2021 | Hassan | A61B 34/25 |
| 2021/0402603 A1* | 12/2021 | Murphy | A61B 34/37 |
| 2022/0022974 A1* | 1/2022 | Beckman | A61B 34/30 |
| 2022/0022976 A1* | 1/2022 | Beckman | A61B 34/30 |
| 2022/0022977 A1* | 1/2022 | Beckman | B25J 15/0213 |
| 2022/0096066 A1* | 3/2022 | Beckman | A61B 34/76 |
| 2022/0096067 A1* | 3/2022 | Beckman | A61B 17/07207 |
| 2022/0096083 A1* | 3/2022 | Beckman | A61B 34/30 |

FOREIGN PATENT DOCUMENTS

| | | | | |
|---|---|---|---|---|
| CN | 103356292 | A | | 10/2013 |
| CN | 105916430 | A | | 8/2016 |
| CN | 108430373 | | * | 10/2016 |
| EP | 2505141 | A1 | | 10/2012 |
| EP | 2526854 | A1 | | 11/2012 |
| EP | 2656778 | A1 | | 10/2013 |
| EP | 2910173 | A1 | | 8/2015 |
| JP | 4063933 | B2 | * | 12/1997 |
| JP | 4063933 | B2 | * | 3/2008 ........... G09B 23/286 |
| JP | 2012-40075 | A | | 3/2012 |
| JP | 2016007355 | | * | 6/2014 |
| JP | 2016-7355 | A | | 1/2016 |
| JP | 2016-67706 | A | | 5/2016 |
| JP | 2016-67775 | A | | 5/2016 |
| JP | 2016-144507 | A | | 8/2016 |
| JP | 2017-839 | A | | 1/2017 |
| WO | WO 2013/065473 | A1 | | 5/2013 |
| WO | WO 2015/040570 | A1 | | 3/2015 |

OTHER PUBLICATIONS

Kron Man, Achia Translation of CN-108430373 Oct. 2016 (Year: 2016).*
Asano T Translation of JP-4063933-B2 Mar. 2008 (Year: 2008).*
Extended European Search Report, dated Feb. 13, 2020, for corresponding European Application No. 18761773.3.
International Preliminary Report on Patentability and Written Opinion of the International Searching Authority (Forms PCT/IB/326, PCT/IB/373 and PCT/ISA/237) for International Application No. PCT/JP2018/006547, dated Sep. 12, 2019, with English translation.
International Search Report (Form PCT/ISA/210) for International Application No. PCT/JP2018/006547, dated May 15, 2018, with English translation.
Chinese Office Action and Search Report for corresponding Chinese Application No. 201880015393.X dated Apr. 6, 2021, with English translation of the Office Action.
Japanese Office Action for corresponding Japanese Application No. 2019-502940, dated Mar. 10, 2020, with English translation.
European Communication pursuant to Article 94(3) EPC for corresponding European Application No. 18761773.3, dated Nov. 22, 2022.

* cited by examiner

ENDOSCOPE SYSTEM, PROCESSOR DEVICE, AND METHOD OF OPERATING ENDOSCOPE SYSTEM

CROSS-REFERENCE TO RELATED APPLICATIONS

This application is a Continuation of PCT International Application No. PCT/JP2018/006547 filed on 22 Feb. 2018, which claims priority under 35 U.S.C § 119(a) to Japanese Patent Application No. 2017-040344 filed on 3 Mar. 2017. The above application is hereby expressly incorporated by reference, in its entirety, into the present application.

BACKGROUND OF THE INVENTION

1. Field of the Invention

The present invention relates to an endoscope system, a processor device, and a method of operating an endoscope system that discriminate a portion having a specific feature, using an endoscope image obtained by imaging an observation target, using an endoscope.

2. Description of the Related Art

In the medical field, diagnosis using an endoscope system comprising a light source device, an endoscope, and a processor device has been performed. In recent years, endoscope systems, which attempt not only to display an endoscope image on display units, such as a monitor but also to discriminate a portion having specific features, such as a lesion, using the endoscope image, have been known. For example, JP2012-040075A discloses an endoscope system that calculates a feature amount, using an endoscope image, and thereafter, discriminates a lesion, using the calculated feature amount.

Additionally, endoscope systems, which perform extraction of blood vessels or the like important for diagnosis, using an endoscope image, have been known. For example, JP2016-144507A discloses an endoscope system that performs blood vessel extraction processing while hanging execution frequency depending on the amount of movement.

SUMMARY OF THE INVENTION

Endoscope systems, which attempt to provide information contributing to diagnosis in addition to the endoscope image by performing discrimination, recognition, or the like of the portion having the specific features, such as a lesion, using the endoscope image as described above, have been known from the past.

However, the processing of performing the determination and the like of the portion having the specific features, such as a lesion, is usually heavy processing that normally requires very high processing capacity. For this reason, it is realistically difficult to continue executing the processing of performing the discrimination or the like of the portion having the specific features, such as a lesion, in real time during observation while continuing consuming the resource of a processor device in large quantities.

Hence, it is realistic that the processing of performing the discrimination or the like of the portion having the specific features, such as a lesion, is appropriately executed as needed depending on a user's request based on button operation or the like. On the other hand, originally, since the operation of endoscope systems is complicated, it is not desirable to put an operational load on users, such as a doctor.

Thus, an object of the invention is to provide an endoscope system, a processor device, and a method of operating an endoscope system capable of suppressing a processing load at a timing when users, such as a doctor, do not desire, and automatically executing processing, such as discrimination, at an appropriate timing when the users, such as a doctor, desire, to acquire information that contributes to diagnosis.

An endoscope system of the invention comprises an image acquisition unit, a discrimination processing unit, and a discrimination processing control unit. The image acquisition unit acquires an endoscope image obtained by imaging an observation target using an endoscope. The discrimination processing unit discriminates a portion having a specific feature in the observation target by performing discrimination processing, using an endoscope image. The discrimination processing control unit controls a start or an end of the discrimination processing on the basis of a change in operation of an endoscope or the endoscope image.

The discrimination processing control unit comprises a feature amount calculation unit and a comparison unit. The feature amount calculation unit calculates a feature amount using the endoscope image. The comparison unit compares the feature amount with a threshold value. In this case, it is preferable that the discrimination processing control unit starts or ends the discrimination processing on the basis of a comparison result in the comparison unit.

It is preferable that the discrimination processing control unit starts or ends the discrimination processing in a case where the endoscope has enlarged or reduced the observation target.

It is preferable that the discrimination processing control unit starts the discrimination processing in a case where illumination light to be used in a case where the endoscope images the observation target is switched to specific illumination light, and ends the discrimination processing in a case where the illumination light to be used in a case where the endoscope images the observation target is switched to illumination light other than the specific illumination light.

It is preferable that the discrimination processing control unit starts the discrimination processing in a case where the illumination light is switched to illumination light with a wavelength of 450 nm or less.

It is preferable that the discrimination processing control unit starts or ends the discrimination processing in a case where an object has passed through a channel inserted through the endoscope.

It is preferable that the discrimination processing control unit starts the discrimination processing in a case where water has passed through the channel.

It is preferable that the discrimination processing control unit starts the discrimination processing in a case where a coloring agent has passed through the channel.

It is preferable that the discrimination processing control unit starts or ends the discrimination processing in a case where a position where the endoscope images the observation target has changed or in a case where the position where the endoscope images the observation target does not change It is preferable that the discrimination processing control unit detects the position where the endoscope images the observation target on the basis of a change of the observation target reflected on the endoscope image.

It is preferable that the discrimination processing control unit detects the position where the endoscope images the observation target, using a position sensor.

It is preferable that the discrimination processing control unit ends the discrimination processing in a case where the position where the endoscope images the observation target has changed.

It is preferable that the discrimination processing control unit starts the discrimination processing on the basis of the change in the operation of the endoscope or the endoscope image, and ends the discrimination processing after a certain preset time has elapsed after the start of the discrimination processing.

It is preferable that the discrimination processing control unit starts or ends the discrimination processing in a case where the endoscope has captured a still image.

It is preferable to further comprise a notification control unit that controls a start or an end of notification of a discrimination result that is a result of the discrimination processing on the basis of the change in operation of the endoscope or the endoscope image.

It is preferable that the notification control unit comprises a feature amount calculation unit that calculates a feature amount using the endoscope image, and a comparison unit that compares the feature amount with a threshold value, and the notification control unit starts or ends the notification of the discrimination result on the basis of a comparison result in the comparison unit.

It is preferable that the notification control unit starts or ends the notification of the discrimination result in a case where the endoscope has enlarged or reduced the observation target.

It is preferable that the notification control unit starts the notification of the discrimination result in a case where illumination light to be used in a case where the endoscope images the observation target is switched to specific illumination light, and ends the notification of the discrimination result in a case where the illumination light to be used in a case where the endoscope images the observation target is switched to illumination light other than the specific illumination light.

It is preferable that the notification control unit starts the notification of the discrimination result in a case where the illumination light is switched to illumination light with a wavelength of 450 nm or less.

It is preferable that the notification control unit starts or ends the notification of the discrimination result in a case where an object has passed through a channel inserted through the endoscope.

It is preferable that the notification control unit starts the notification of the discrimination result in a case where water has passed the channel.

It is preferable that the notification control unit starts the notification of the discrimination result in a case where a coloring agent has passed through the channel.

It is preferable that the notification control unit starts or ends the notification of the discrimination result in a case where a position where the endoscope images the observation target has changed or in a case where the position where the endoscope images the observation target does not change.

It is preferable that the notification control unit detects the position where the endoscope images the observation target on the basis of a change of the observation target reflected on the endoscope image.

It is preferable that the notification control unit detects the position where the endoscope images the observation target, using a position sensor.

It is preferable that the notification control unit ends the notification of the discrimination result in a case where the position where the endoscope images the observation target has changed.

It is preferable that the discrimination processing control unit starts the notification of the discrimination result on the basis of the change in the operation of the endoscope or the endoscope image, and ends the notification of the discrimination result after a certain preset time has elapsed after the start of the notification of the discrimination result.

It is preferable that the notification control unit starts or ends the notification of the discrimination result in a case where the endoscope has captured a still image.

It is preferable that the notification control unit provides the notification of the discrimination result, using any of voice, an image, a message, or a combination thereof.

A processor device of the invention comprises an image acquisition unit, a discrimination processing unit, and a discrimination processing control unit. The image acquisition unit acquires an endoscope image obtained by imaging an observation target using an endoscope. The discrimination processing unit discriminates a portion having a specific feature in the observation target by performing discrimination processing, using an endoscope image. The discrimination processing control unit controls a start or an end of the discrimination processing on the basis of a change in operation of an endoscope or the endoscope image.

A method of operating an endoscope system of the invention comprises a step of acquiring an endoscope image, which is obtained by imaging an observation target using an endoscope, using an image acquisition unit; and a step of discriminating a portion having a specific feature in the observation target by performing discrimination processing using the endoscope image, using a discrimination processing unit. The method of operating an endoscope system of the invention comprises a step of controlling a start or an end of the discrimination processing on the basis of a change in operation of the endoscope or the endoscope image, using the discrimination processing control unit.

According to the endoscope system, the processor device, and the method of operating an endoscope system, it is possible to suppress a processing load at a timing when users, such as a doctor, do not desire, and automatically executing processing, such as discrimination, at an appropriate timing when the users, such as a doctor, desire, to acquire information that contributes to diagnosis.

DESCRIPTION OF THE PREFERRED EMBODIMENTS

First Embodiment

Figure 1:
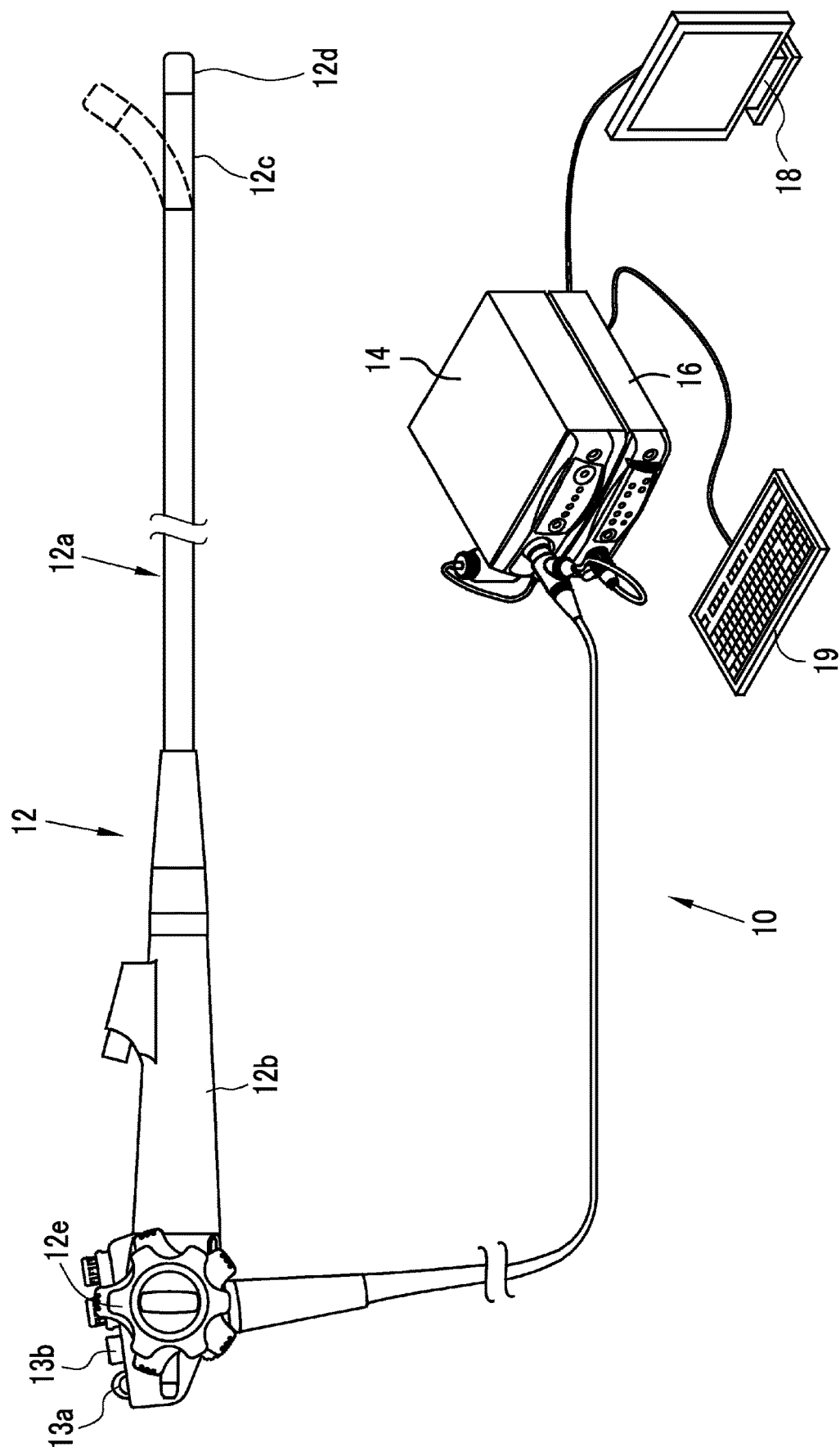
FIG. 1 is an external view of an endoscope system.

As illustrated in FIG. 1, an endoscope system 10 comprises an endoscope 12, a light source device 14, a processor device 16, a monitor 18, and a console 19. The endoscope 12 images an observation target. The light source device 14 generates illumination light. The processor device 16 performs system control, image processing, and the like of the endoscope system 10. The monitor 18 is a display unit that displays a display image (hereinafter, referred to as an endoscope image; for example, refer to an endoscope image 101 of FIG. 5 and an endoscope image 102 of FIG. 6) generated by the processor device 16. The console 19 is an input device that performs setting input and the like to the processor device 16 and the like.

The endoscope 12 has an insertion part 12a to be inserted into a subject, an operating part 12b provided at a proximal end portion of the insertion part 12a, a bending part 12c provided on a distal end side of the insertion part 12a, and a distal end part 12d. By operating an angle knob 12e of the operating part 12b, the bending part 12c is bent. As the bending part 12c is bent, the distal end part 12d is directed in a desired direction. In addition, the distal end part 12d is provided with a forceps port (not illustrated) that allows treatment tools, such as forceps, to be protruded toward the observation target therethrough, or a jet port (not illustrated) that allows air, water, and the like to be jetted toward the observation target therethrough.

Additionally, the operating part 12b is provided with a zoom operating part 13a, a mode changeover switch 13b, and the like in addition to the angle knob 12e. By operating the zoom operating part 13a, the observation target can be enlarged or reduced for imaging. Observation modes can be switched by the operation of the mode changeover switch 13b. The endoscope system 10 has, for example, a plurality of observation modes, such as a normal observation mode in which the observation target is observed in natural tone, using white light for the illumination light, and a special observation mode in which blood vessels or the like in a mucous membrane surface layer are enhanced. By operating the mode changeover switch 13b, the plurality of observation modes can be appropriately changed at optional timings.

Figure 2:
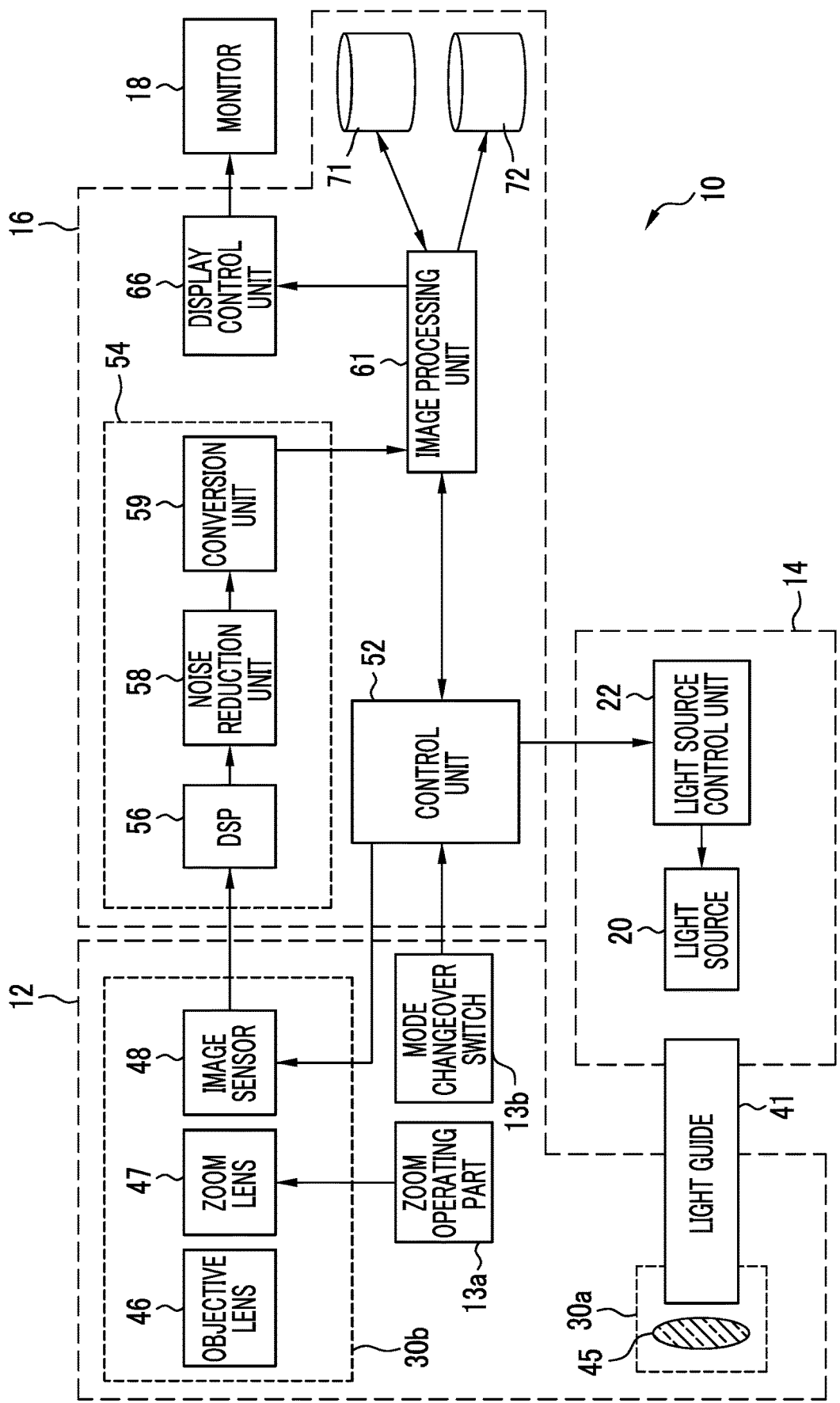
FIG. 2 is a block diagram of an endoscope system.

As illustrated in FIG. 2, the light source device 14 comprises a light source unit 20 that emits the illumination light, and a light source control unit 22 that controls driving of the light source unit 20.

The light source unit 20 comprises, for example, a plurality of light emitting diodes (LEDs) that emit light having different central wavelengths or wavelength ranges (hereinafter, simply referred to as "having different wavelengths") as light sources, and a plurality of kinds of illumination light beams having different wavelengths can be emitted depending on light emission or turn-on of the respective LEDs, adjustment of light quantity, and the like. For example, the light source unit 20 can emit broadband purple light, blue light, green light, and red light with relatively wide wavelength ranges as the illumination light beams, respectively. Moreover, the light source unit 20 can emit narrowband (meaning that the wavelength ranges are ranges of about 10 nm to 20 nm) purple light, blue light, green light, and red light as the illumination light beams, in addition to the broadband purple light, blue light, green light, and red light.

In addition, instead of the LEDs, a combination of a laser diode (LD), a fluorescent body, and a band limiting filter, a combination of a lamp, such as a xenon lamp, and a band limiting filter, or the like can be used for the light source unit 20. Even in a case where the LEDs constitute the light source unit 20, the fluorescent body or the band limiting filter can be used in combination with the LEDs.

The light source control unit 22 independently controls the timing of ON/OFF of the respective light sources that constitute the light source unit 20, the light emission amount thereof at the time of ON, and the like. As a result, the light source unit 20 can emit the plurality of kinds of illumination light beams with different wavelengths. Additionally, the light source control unit 22 controls the light source unit 20 in conformity with timing (so-called frame) for imaging of an image sensor 48.

The illumination light emitted from the light source unit 20 is incident on a light guide 41. The light guide 41 is built within the endoscope 12 and a universal cord, and propagates illumination light up to the distal end part 12d of the endoscope 12. The universal cord is a cord that connects the endoscope 12, and the light source device 14 and the processor device 16 together. In addition, multi-mode fiber can be used as the light guide 41. As an example, a fine-diameter fiber cable of which the core diameter is 105 μm, the clad diameter is 125 μm, and a diameter including a protective layer serving as an outer cover is (φ0.3 to 0.5 mm can be used.

The distal end part 12d of the endoscope 12 is provided with an illumination optical system 30a and an imaging optical system 30b. The illumination optical system 30a has an illumination lens 45, and emits the illumination light toward the observation target via the illumination lens 45. The imaging optical system 30b has an objective lens 46, a zoom lens 47, and an image sensor 48. The image sensor 48 images the observation target, using reflected light or the like (including scattered light, fluorescence emitted from the observation target, fluorescence resulting from medicine administered to the observation target, or the like in addition to the reflected light) of the illumination light returning from the observation target via the objective lens 46 and the zoom lens 47. The zoom lens 47 is moved by operating the zoom operating part 13a, and enlarges or reduces the observation target to be imaged using the image sensor 48.

The image sensor 48 is, for example, a color sensor having color filters of a primary color system, and comprises three types of pixels of a B pixel (blue pixel) having a blue color filter, a G pixel (green pixel) having a green color filter, and an R pixel (red pixel) having a red color filter. The blue color filter allows mainly purple to blue light to be transmitted therethrough. The green color filter allows mainly green light to be transmitted therethrough. The red color filter allows mainly red light to be transmitted therethrough. In a case where the observation target of the primary color system is imaged using the image sensor 48 as described above, three types of images including a B image (blue image) obtained from the B pixel, a G image (green image) obtained from the G pixel, and an R image (red image) obtained from the R pixel can be simultaneously obtained to the maximum.

In addition, as the image sensor 48, a charge coupled device (CCD) image sensor or a complementary metal-oxide semiconductor (CMOS) image sensor is available. Additionally, although the image sensor 48 of the present embodiment is the color sensor of the primary color system, a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the above respective color pixels in a case where the color sensor of the complementary color system is used can be converted into the B image, the G image, and the R image in a case where complementary color-primary color conversion is performed. Additionally, instead of the color sensor, a monochrome sensor that is not provided with the color filters can be used as the image sensor 48. In this case, the above respective color images can be obtained by sequentially imaging the observation target, using the respective illumination light beams in colors, such as BGR.

The processor device 16 has a control unit 52, an image acquisition unit 54, an image processing unit 61, and a display control unit 66.

The control unit 52 performs overall control of the endoscope system 10, such as synchronous control between radiation timing of the illumination light and timing of the imaging. For example, the control unit 52 performs synchronous control of the radiation timing of the illumination light, the timing of the imaging, and the like. Additionally, in a case where the zoom operating part 13*a* is operated, there is a case where the control unit 52 receives an operation signal from the zoom operating part 13*a* and inputs, to the image processing unit 61, a control signal (hereinafter referred to as an imaging size signal) showing the imaging size (that is, enlargement or reduction of the observation target, the degree thereof) of the observation target. In the image processing unit 61, there is a case where whether or predetermined processing is performed, the intensity of the predetermined processing is adjusted, or the like on the basis of the imaging size signal and depending on the imaging size of the observation target.

Additionally, in a case where the mode changeover switch 13*b* is operated, the control unit 52 receives an operation signal from the mode changeover switch 13*b*, and inputs a control signal (hereinafter referred to as an observation mode specification signal) for specifying an observation mode to the light source control unit 22 and the image processing unit 61. The observation mode specification signal to be input to the light source control unit 22 and the image processing unit 61 by the control unit 52 specifies the type, light emission order, and the like of illumination light to be used. The light source control unit 22 emits the illumination light in accordance with the observation mode specification signal, using the light source unit 20. In the image processing unit 61, there is a case where whether or not predetermined processing is performed, the intensity of the predetermined processing, is adjusted, or the like on the basis of the observation mode specification signal and depending on the imaging size of the observation target.

The image acquisition unit 54 acquires an image of the observation target from the image sensor 48. The image of the observation target that the image acquisition unit 54 acquires from the image sensor 48 is an endoscope image. In addition, an image to be generated for display using the image of the observation target acquired from the image sensor 48 is also an endoscope image. Hereinafter, in a case where distinction is required, the image of the observation target acquired from the image sensor 48 is referred to as an "captured endoscope image" or simply an "image", and the image generated for display is referred to as an "display endoscope image" or simply an "endoscope image", In the present embodiment, the image sensor 48 has the color filters. Thus, the image acquisition unit 54 acquires an image (captured endoscope image) for each illumination light beam and for color filter.

The image acquisition unit 54 has a digital signal processor (DSP) 56, a noise reduction unit 58, and a conversion unit 59, and performs various kinds of processing on an acquired image, as needed, using these units.

The DSP 56 performs various kinds of processing, such as defect correction processing, offset processing, gain correction processing, linear matrix processing, gamma conversion processing, demosaicing processing, and YC conversion processing, on the acquired image, as needed.

The defect correction processing is the processing of correcting the pixel value of a pixel corresponding to a defective pixel of the image sensor 48. The offset processing is the processing of reducing a dark current component from the images subjected to the defect correction processing, and setting an accurate zero level. The gain correction processing is the processing of adjusting a signal level of each image by multiplying the images subjected to the offset processing by a gain. The linear matrix processing is the processing of enhancing color reproducibility on the images subjected to the offset processing, and the gamma conversion processing is the processing of adjusting the brightness and saturation of the images after the linear matrix processing. The demosaicing processing (also referred to as equalization processing or synchronization processing) is the processing of interpolating the pixel value of a missing pixel, and is performed on the images after the gamma conversion processing. The missing pixel is a pixel with no pixel value due to the arrangement of the color filters (because other color pixels are arranged in the image sensor 48). For example, since the B image is an image obtained by imaging the observation target in the B pixel, there is no pixel value in pixels at positions corresponding to the G pixel and the R pixel. In the demosaicing processing, the pixel values of the pixels at the positions of the G pixel and the R pixel of the image sensor 48 are generated by interpolating the B image. The YC conversion processing is the processing of converting the images after the demosaicing processing into a luminance channel Y, a color difference channel Cb, and a color difference channel Cr.

The noise reduction unit 58 performs noise reduction processing using, for example, a moving average method, a median filter method, or the like, on the luminance channel Y, the color difference channel Cb, and the color difference channel Cr. The conversion unit 59 re-converts the luminance channel Y, the color difference channel Cb, and the color difference channel Cr after the noise reduction processing into images in respective colors of BGR.

Figure 3:
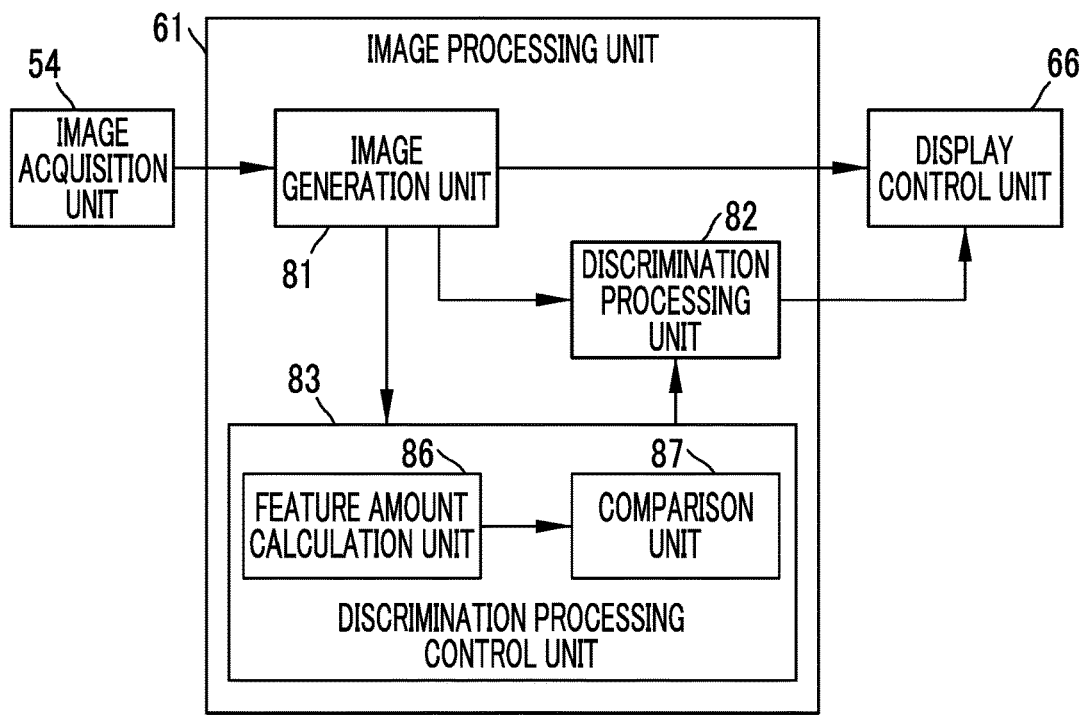
FIG. 3 is a block diagram of an image processing unit.

The image processing unit 61 generates an endoscope image to be displayed on the monitor 18, using the images acquired by the image acquisition unit 54. Additionally, the image processing unit 61 performs the discrimination processing of discriminating a portion having a specific feature of the observation target, using the endoscope image, as needed. For these, as illustrated in FIG. 3, the image processing unit 61 comprises an image generation unit 81, a discrimination processing unit 82, and a discrimination processing control unit 83.

The image generation unit 81 generates an endoscope image according to an observation mode, using the images acquired by the image acquisition unit 54. In a case where an observation mode is the normal observation mode, the image generation unit 81 generates an endoscope image capable of observing the observation target in natural tone. Additionally, in a case where an observation mode is the special observation mode, an endoscope image according to the purpose of the special observation mode is generated, for example, by using a combination of images different from that of the normal observation mode, performing a method of assigning an image to be used to a color channel different from that of the normal observation mode, or the like. For example, an endoscope image in which the blood vessels in the mucous membrane surface layer or the like are enhanced is generated.

In addition, in a case where an endoscope image according to an observation mode is generated, the image processing unit 61 performs color conversion processing, color enhancement processing, and structure enhancement processing, on the images acquired by the image acquisition unit 54, as needed. In the color conversion processing, 3×3 matrix processing, gradation transformation processing, three-dimensional look-up table (LUT) processing, and the like are performed on the images in the respective colors of BGR. The color enhancement processing is the processing of enhancing the colors of an image, and the structure enhancement processing is the processing of enhancing, for example, the tissue or structure of the observation target, such as blood vessels or pit patterns.

The discrimination processing unit 82 discriminates a portion (hereinafter referred to as a specific portion) having a specific feature in the observation target by performing discrimination processing, using the endoscope image generated by the image generation unit 81. The "specific portion" is a portion capable of being distinguished from other portions (for example, normal mucous membranes) on the basis of the presence or absence, shape (thickness, length, the state of an edge that is a boundary with other tissue, the disorder of tissue or the like, the degree of meandering of linear tissue or the like), distribution, or color of tissue or structure, or the state (for example, the depth under the mucous membrane, or situations of internal parameters, such as the oxygen saturation of the hemoglobin included in blood vessels) of tissue or structure. The "specific feature" that determines the specific portion is a feature that allows a perform to view and understand an endoscope image as described above, an endoscope image, or information obtained by calculation using images to be used to generate the endoscope image. Hereinafter, information, such as quantity regarding the specific feature that defines the specific portion, is relates to as "feature amount".

The "discrimination" means obtaining information that further contributes to diagnosis on the basis of the features of the specific portion or the like, and the "discrimination processing" means the processing that the discrimination processing unit 82 performs for discrimination. For example, the recognition processing of recognizing whether or not the specific portion is a lesion on the basis of the feature amount showing the feature of the specific portion is the discrimination processing. Additionally, the discrimination processing also includes the processing of calculating information that suggests a possibility of being a lesion, such as an index indicating a possibility that the specific portion is a lesion, on the basis of the feature amount showing the feature of the specific portion. Moreover, in a case where the specific portion is a lesion, the processing of performing recognition of the type, classification, benignity, or malignancy of the lesion, or recognition of the progress degree or invasiveness of the lesion, or the like is also discrimination processing.

The discrimination processing unit 82 performs the above discrimination processing by using, for example, a convolution neural network (CNN) 71 that is learned in a specific task (more specifically, specific classification) in advance (refer to FIG. 2), a neural network, a support vector machine (SVM), an adaptive boosting (AdaBoost), or the like. A result (hereinafter referred to as a discrimination result) of the discrimination processing is, for example, "whether or not the specific portion is a lesion" (including information capable of discriminating whether or not the specific portion is a lesion). Hence, in a case where the specific portion is a lesion, the recognition of the type, classification, benignity, or malignancy of the lesion, or the recognition of the progress degree or invasiveness of the lesion, or the like is the discrimination result. Additionally, a score showing the probability of discrimination of whether or not the specific portion is a lesion or the probability of the classification or the like of the above lesion can be the discrimination result. In the present embodiment, the discrimination processing unit 82 discriminates whether or not the specific portion is a lesion, and sets a score showing the probability of the discrimination as the discrimination result. The score is, for example, a numerical value of 0.0 to 1.0. Additionally, the discrimination processing unit 82 stores information on an endoscope image used for discrimination processing in the storage unit 72 (refer to FIG. 2) in a case where the discrimination processing is performed. The information on the endoscope image used for the discrimination processing is a frame number, the score that is the discrimination result, or the like in addition to the endoscope image itself. The discrimination processing unit 82 associates the endoscope image, the frame number, the score that is the discrimination result, and the like in the storage unit 72 in association with each other. The storage unit 72 is, for example, a storage, such as a memory or a hard disk.

In addition, although the discrimination processing unit 82 uses the endoscope image (display endoscope image) generated by the image generation unit 81 for the discrimination processing, the display endoscope image is generated using the generated endoscope image. Hence, the discrimination processing unit 82 performs the discrimination processing, using the endoscope image obtained by imaging the observation target using an endoscope as a result. Additionally, the discrimination processing unit 82 can perform the discrimination processing, using the captured endoscope image, directly instead of the display endoscope image.

The discrimination processing control unit 83 controls the start or the end of the discrimination processing in the discrimination processing unit 82 on the basis of a change in the operation of the endoscope 12, or the endoscope image. The "change in the operation of the endoscope 12" means transition or switching of the operation aspect of the endoscope 12, and transition or switching of the operation aspect without a direct relation with the discrimination processing. For example, enlargement or reduction of the observation target, switching of the illumination light resulting from switching of the observation modes, or the like is the change in the operation of the endoscope 12. The "on the basis of the endoscope image" means, for example, being based on a change in feature of the observation target reflected on the endoscope image or being based on a change in the feature amount.

In addition, the "start of the discrimination processing" means that, in a case where the discrimination processing is performed on an endoscope image of a certain optional frame, the discrimination processing is performed on endoscope images of at least one or more frames subsequent thereto. That is, the "start of the discrimination processing" also includes a case where the discrimination processing is performed only on an endoscope image equivalent to one frame while frames in which the discrimination processing is performed continue. Additionally, the "end of the discrimination processing" means that, in a case where the discrimination processing is performed on an endoscope image of a certain optional frame, the discrimination processing is not performed on endoscope images of at least one or more frames subsequent thereto. That is, the "end of the discrimination processing" also includes a case where the discrimination processing is not performed only on an endoscope image equivalent to one frame while frames in which the discrimination processing is not performed continue.

In the present embodiment, the discrimination processing control unit 83 controls the start and end of the discrimination processing in the discrimination processing unit 82 on the basis of the endoscope image. Therefore, the discrimination processing control unit 83 comprises a feature amount calculation unit 86 and a comparison unit 87.

The feature amount calculation unit 86 acquires the endoscope image from the image generation unit 81. Then, the feature amount calculation unit 86 calculates the feature amount of the observation target reflected on the endoscope image, using the acquired endoscope image. The calculation of the feature amount is performed on endoscope images of some (for example, every several frames or the like) or all frames to be generated by the image generation unit 81. Additionally, the feature amount calculation unit 86 calculates feature amounts of all or some endoscope images.

The comparison unit 87 compares the feature amount calculated by the feature amount calculation unit 86 with a preset feature amount of an endoscope image obtained by imaging a normal observation target. A result (hereinafter referred to as a comparison result) of the comparison performed by the comparison unit 87 shows whether or not the value of the feature amount calculated by the feature amount calculation unit 86 or the distribution of the value is within a normal range, and shows a change in feature of the observation target reflected on endoscope images that are sequentially acquired. In the present embodiment, the comparison unit 87 sets the preset feature amount of the endoscope image obtained by imaging the normal observation target as a threshold value, and compares the calculated feature amount that the feature amount calculation unit 86 with the threshold value. The comparison between the feature amount and the threshold value is sequentially performed whenever the feature amount calculation unit 86 calculates the feature amount. The case where the feature amount is equal to more than the threshold value is, for example, a case where the redness or the like is reflected on an endoscope image, or the like, and is a case where performing the discrimination processing is basically desired. On the contrary, the case where the feature amount becomes less than the threshold value is, for example, a case where there is no redness or the like, the observation target is normal, and it is basically unnecessary to perform the discrimination processing.

The discrimination processing control unit 83 starts or ends the discrimination processing on the basis of the comparison result of the comparison unit 87. Accordingly, as a result, the discrimination processing control unit 83 controls the start or the end of the discrimination processing in the discrimination processing unit 82 on the basis of the endoscope image. More specifically, in the present embodiment, the discrimination processing is started in a case where the feature amount becomes equal to or more than the threshold value, and ends the discrimination processing in a case where the feature amount becomes less than the threshold value. As a result, the discrimination processing unit 82 executes the discrimination processing automatically in a case where in a case where the feature amount is equal to or more than the threshold value, and automatically ends the discrimination processing in a case where the feature amount becomes less than the threshold value.

The display control unit 66 acquires the endoscope image from the image processing unit 61, and converts the acquired endoscope image in a form suitable for display to sequentially output and display converted images on the monitor 18. Accordingly, a doctor or the like can observe the observation target, using the endoscope image. Additionally, in a case where the discrimination processing unit 82 performs the discrimination processing, the display control unit 66 acquires the score that is the discrimination result from the discrimination processing unit 82 in addition to the endoscope image. Then, the score that is the discrimination result is displayed on the monitor 18 together with the endoscope image.

Figure 4:
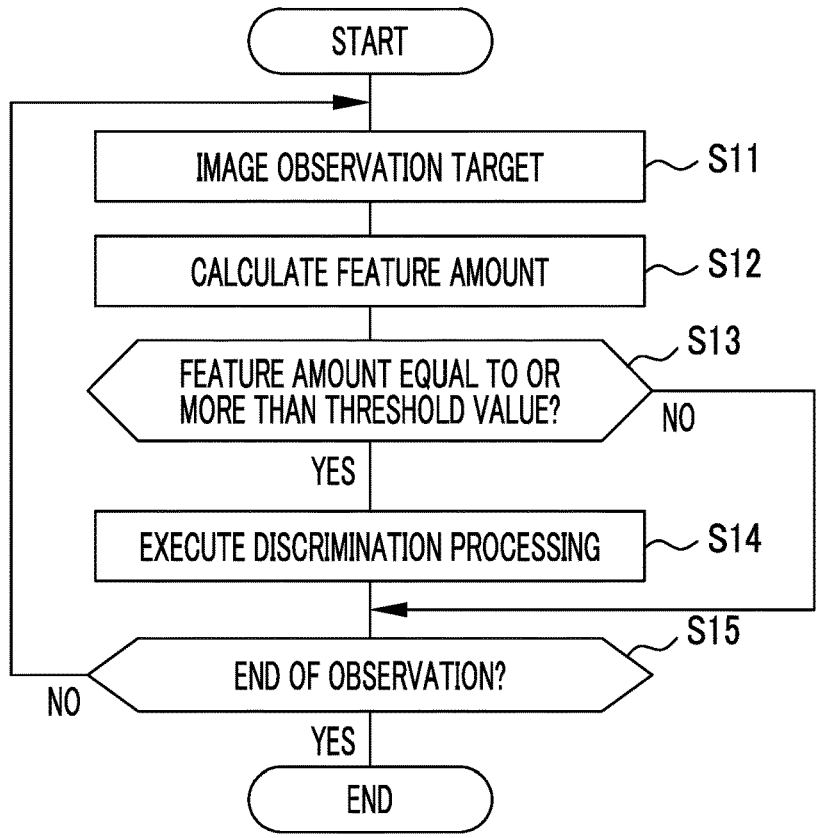
FIG. 4 is a flowchart illustrating a flow of start and end of discrimination processing.

Next, a flow of the start and end of the discrimination processing in the endoscope system 10 will be described along the flowchart illustrated in FIG. 4. First, an observation mode is selected, and an observation target is imaged (S11). Accordingly, the image acquisition unit acquires a captured endoscope image from the image sensor 48, and the image generation unit 81 generates a display endoscope image, using the captured endoscope image.

Figure 5:
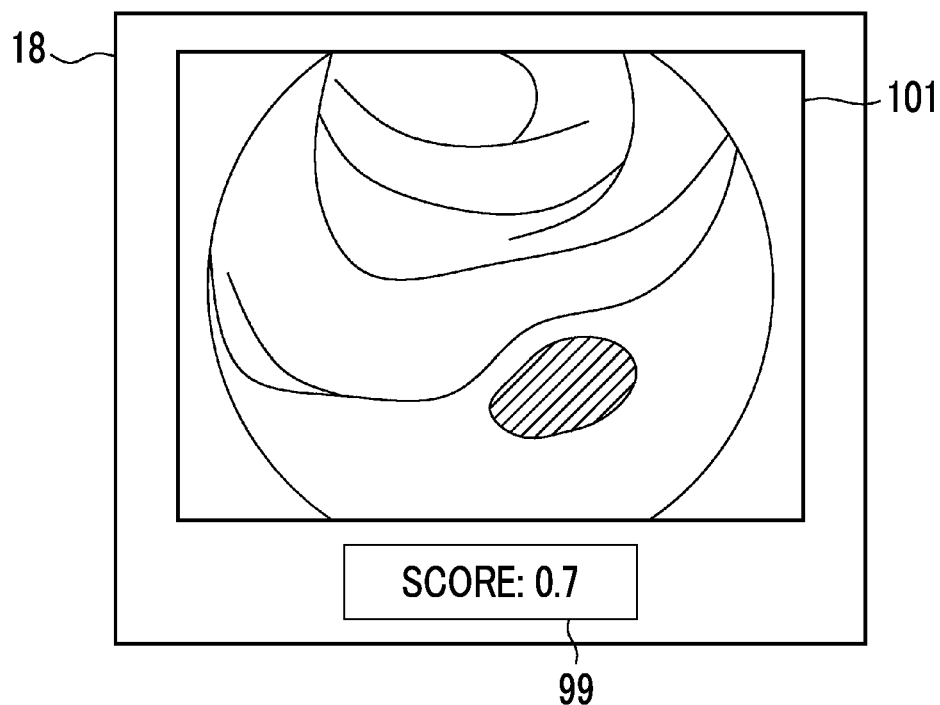
FIG. 5 is an example of display in a case where the discrimination processing is performed.

In a case where the endoscope image is acquired, the discrimination processing control unit 83 calculates a feature amount in the feature amount calculation unit 86 (S12), and thereafter, compares the feature amount with a threshold value in the comparison unit 87 (S13). In a case where the feature amount becomes equal to or more than the threshold value as a result of the comparison in the comparison unit 87 (S13: YES), the discrimination processing control unit 83 executes the discrimination processing in the discrimination processing unit 82 (S14). Usually, an imaging rate is sufficiently faster than the change of the endoscope image. Thus, once the feature amount becomes equal to or more than the threshold value, the feature amount becomes equal to or more than the threshold value for a while after that. For this reason, as the feature amount becomes substantially equal to or more than the threshold value, the discrimination processing starts. In a case where the discrimination processing starts, as illustrated in FIG. 5, the display control unit 66 serially display the endoscope image 101 used for the discrimination processing, and the score 99, which is the discrimination result, on the monitor 18.

Figure 6:
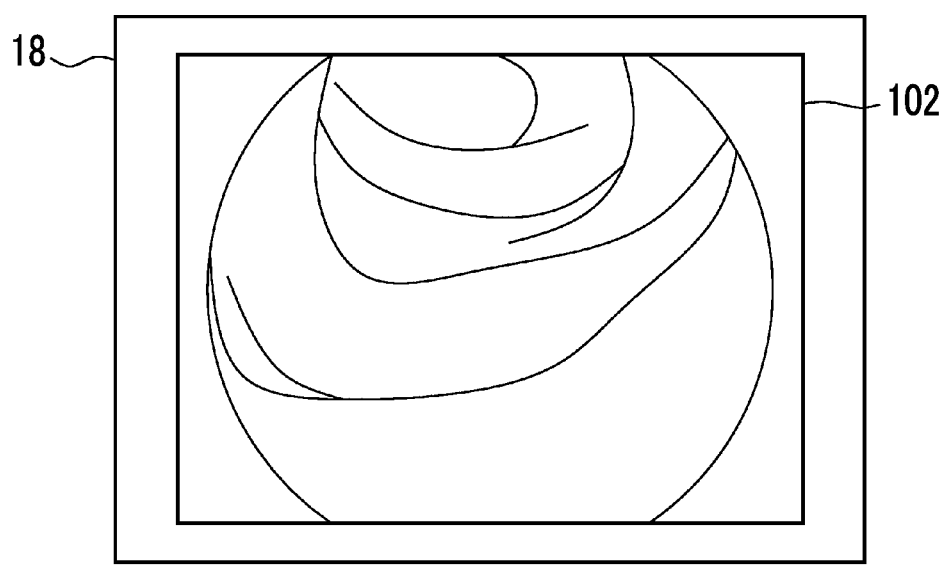
FIG. 6 is an example of display in a case where the discrimination processing is not performed.

On the other hand, in a case where the feature amount is less than the threshold value as a result of the comparison in the comparison unit 87 (S13: NO), the discrimination processing control unit 83 skips the discrimination processing in the discrimination processing unit 82. Usually, the imaging rate is sufficiently faster than the change of the endoscope image. Thus, once the feature amount becomes less than the threshold value, the feature amount becomes less than the threshold value for a while after that. For this reason, as the feature amount becomes substantially less than the threshold value, the discrimination processing ends. After the discrimination processing ends, as illustrated in FIG. 6, the display control unit 66 serially displays the endoscope image 102, on which the discrimination processing is not performed, on the monitor 18.

Then, the start and end of the above discrimination processing are repeatedly performed till the end of the observation (S15). For this reason, while the feature amounts of endoscope images to be sequentially generated are sequentially calculated and the calculated feature amounts are sequentially compared with the threshold value, in a case where a feature amount becomes equal to or more than the threshold value from a state where the feature amount is less than the threshold value, even in a case where a button operation or the like is not performed, the discrimination processing can be automatically started, and the score that is the discrimination result can be provided for a doctor or the like so as to support diagnosis. Additionally, in a case where the feature amount becomes less than the threshold value and the necessity for the discrimination processing fades from a state where the discrimination processing is once started, even in a case where a button operation or the like is not performed, the discrimination processing can be automatically ended, and the processing load (consumption of resources, such as a memory) of the processor device 16 can be suppressed.

Second Embodiment

In the above first embodiment, the discrimination processing control unit 83 starts and ends the discrimination processing on the basis of a change (change of the endoscope image) in the feature amount. Instead of this, however, in a case where the endoscope 12 enlarges or reduces the observation target, the discrimination processing can be started or ended.

Figure 7:
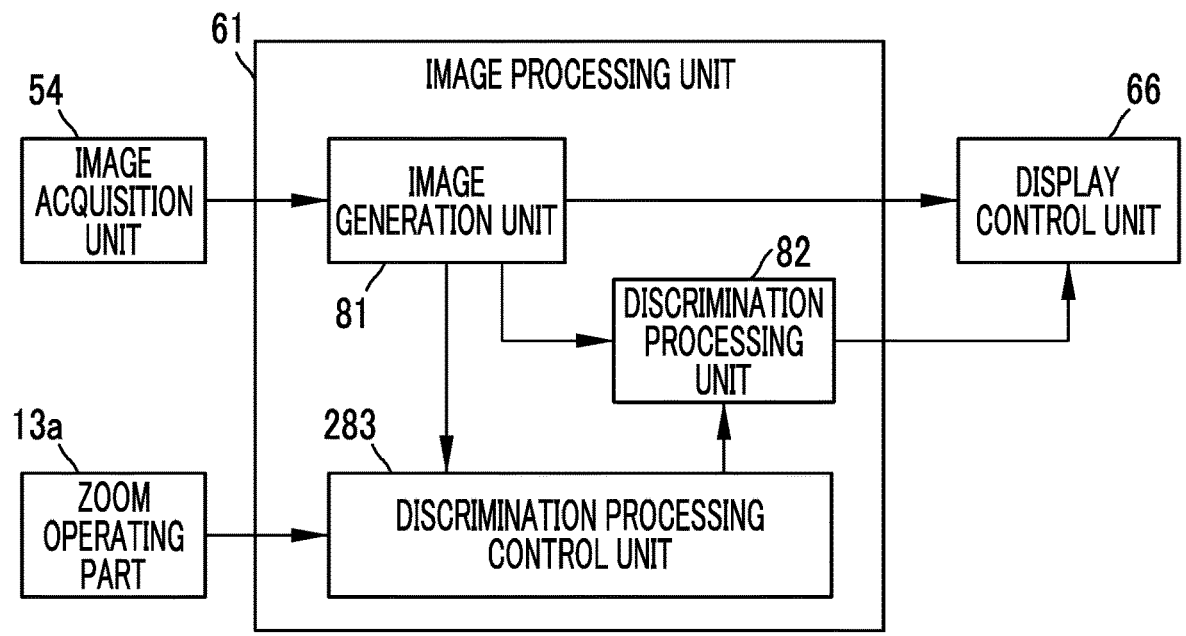
FIG. 7 is a block diagram of an image processing unit in a second embodiment.

In this case, as illustrated in FIG. 7, the image processing unit 61 is provided with the discrimination processing control unit 283 instead of the discrimination processing control unit 83 of the first embodiment. The discrimination processing control unit 283 acquires information on the operation status of the zoom operating part 13a via the control unit 52. Specifically, the discrimination processing control unit 283 acquires an imaging size signal showing the imaging size of the observation target. Then, the discrimination processing is started or ended on the basis of the presence or absence of the enlargement or reduction of the observation target known from the imaging size signal or the degree thereof.

Figure 8:
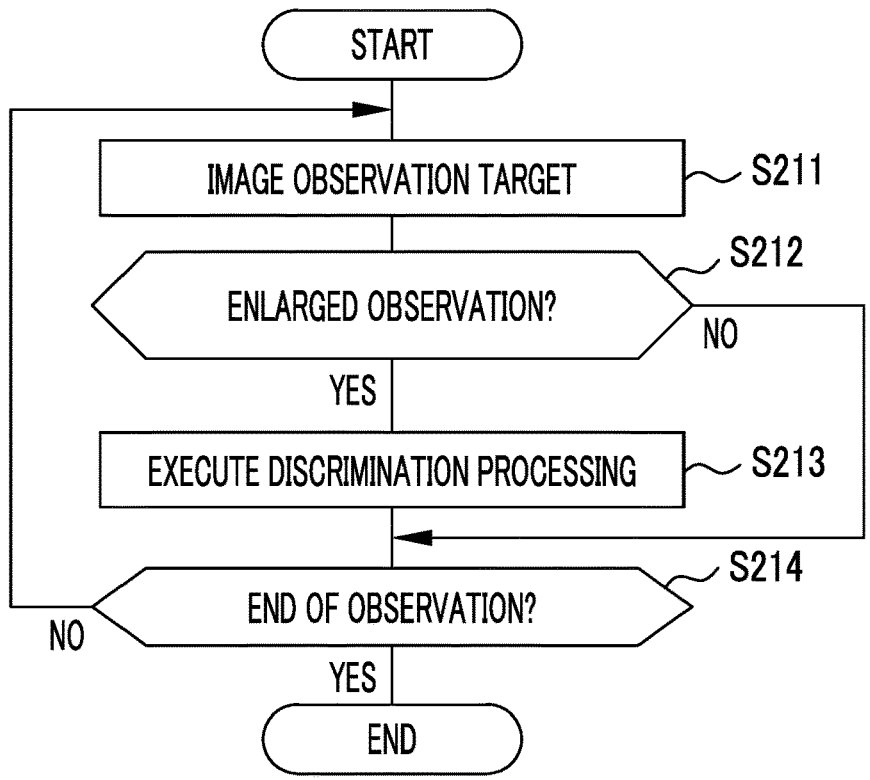
FIG. 8 is a flowchart illustrating a flow of start and end of discrimination processing in the second embodiment.

For example, as illustrated in FIG. 8, in a case where the observation target is imaged (S211) and an endoscope image is acquired, the discrimination processing control unit 283 detects whether or not the observation target is enlarged and observed on the basis of the imaging size signal (S212).

Then, in a case where the enlargement and observation are performed (S212: YES), the discrimination processing control unit 83 executes the discrimination processing in the discrimination processing unit 82 (S213). In a case where the discrimination processing is not being executed in the immediately preceding frame, this substantially becomes a start of the discrimination processing. On the other hand, in a case where the enlargement and observation are not performed (S212: NO), the discrimination processing control unit 283 skips the discrimination processing in the discrimination processing unit 82. In a case where the discrimination processing is being executed in the immediately preceding frame, this substantially becomes an end of the discrimination processing.

By repeating the above operation till the end of the observation (S214), the discrimination processing is automatically performed while the enlargement and observation are performed, and the discrimination processing also automatically ends in an interlocking manner in a case where the enlargement and observation ends. This is because a doctor or the like enlarges and observes the observation target in a case where an enlarged portion is a lesion or there is a possibility that the enlarged portion is a lesion. Hence, in a case where the discrimination processing is started and ended on the basis of the presence or absence of enlargement as described above, the discrimination processing can be performed at an appropriate timing when a doctor or the like desires the discrimination processing, and provide the score 99 that is the discrimination result. Then, the processing load on the processor device 16 can be suppressed without vainly performing the discrimination processing at unnecessary timings.

In the above second embodiment, the discrimination processing control unit 283 starts the discrimination processing in a case where the observation target is enlarged. However, contrary to this, in a case where the observation target is reduced, the discrimination processing can be started. The observation target is reduced and the observation target is imaged by so-called "pulling", for example, in a case where the presence or absence of a portion with the possibility of a lesion or a lesion is confirmed. In this case, in a case where the discrimination processing is performed and the score that is the discrimination result is displayed, it can be easily confirmed whether or not there is any portion with a lesion or the possibility of a lesion within an observation range.

In the above second embodiment and the above modification example, in a case where the observation target is enlarged or reduced, the discrimination processing is started. However, the discrimination processing can be started or ended on the basis of the degree of enlargement or reduction of the observation target, as in a case where the observation target is enlarged to be equal to more than a specific enlargement ratio, in a case where the observation target is reduces to be equal to or less than a specific reduction ratio, or in a case where the enlargement ratio (reduction ratio) is within a specific range.

In the above second embodiment and the above modification example, the discrimination processing control unit 283 starts or ends the discrimination processing on the basis of the imaging size signal showing the operation status of the zoom operating part 13a. However, the discrimination processing control unit 283 can detect the enlargement or reduction of the observation target or the degree thereof, using the endoscope image instead of the imaging size signal, and can start or end the discrimination processing on the basis of the detection result. In this case, the discrimination processing control unit 283 acquires the endoscope image from the image acquisition unit 54 or the image generation unit 81, and stores endoscope images of at least one past frame. Then, in a case where an endoscope image is newly acquired, the newly acquired endoscope image is compared with the stored past endoscope images, and the enlargement or reduction of the observation target or the degree thereof is detected. In this case, the discrimination processing control unit 283 also functions as an enlargement and reduction detection unit that detects the enlargement or reduction of the observation target or the degree thereof.

Third Embodiment

The endoscope system 10 can start or end the discrimination processing on the basis of "the change in the operation of the endoscope 12 or the endoscope image" different from the above first embodiment and second embodiment. For example, the discrimination processing can be started or ended, for example, in a case where there is switching of the observation modes, that is, the illumination light to be used in a case where the endoscope 12 images the observation target is switched.

Figure 9:
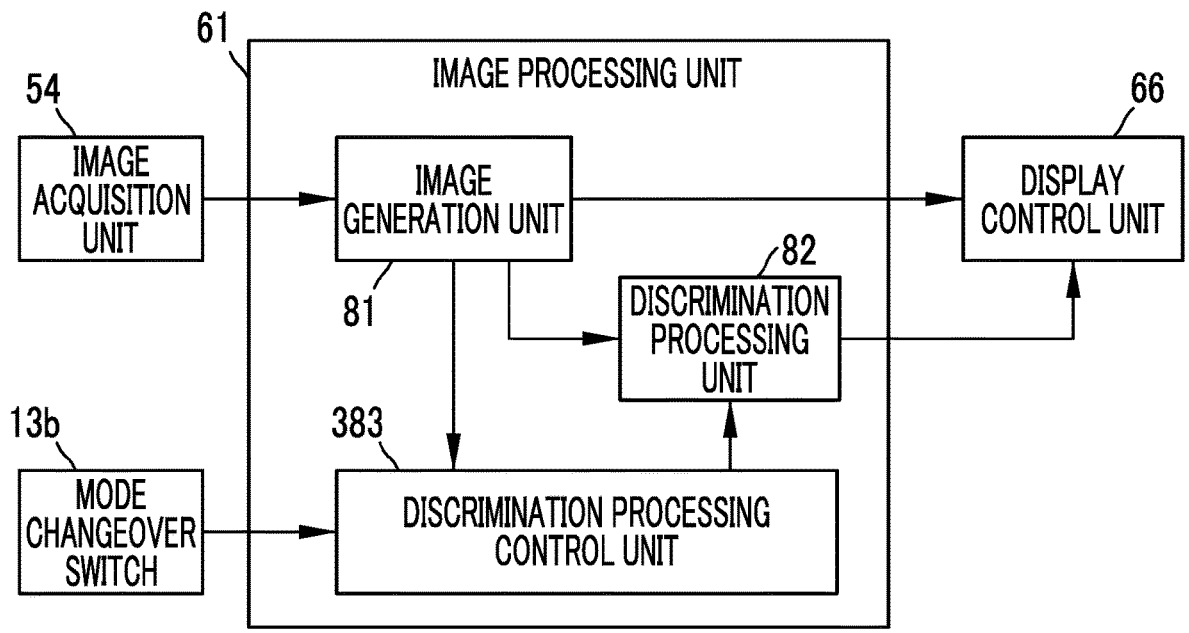
FIG. 9 is a block diagram of an image processing unit in a third embodiment.

In this case, as illustrated in FIG. 9, the image processing unit 61 is provided with a discrimination processing control unit 383 instead of the discrimination processing control unit 83 of the first embodiment or the discrimination processing control unit 283 of the second embodiment. The discrimination processing control unit 383 acquires the information on the operation status of the mode changeover switch 13b via the control unit 52. Specifically, the discrimination processing control unit 383 acquires a observation mode specification signal that specifies an observation mode. Then, from the type of the observation mode specified by the observation mode specification signal, the switching of the illumination light is detected and the discrimination processing is started or ended.

Figure 10:
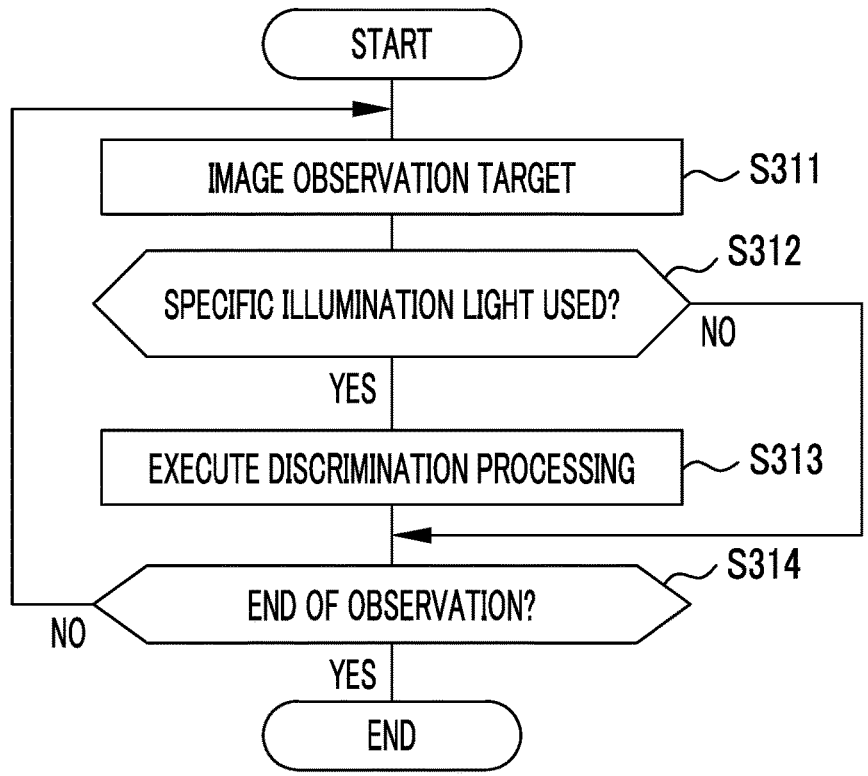
FIG. 10 is a block diagram of an image processing unit in a third embodiment.

For example, as illustrated in FIG. 10, in a case where the observation target is imaged (S311) and an endoscope image is acquired, the discrimination processing control unit 383 detects whether or not specific illumination light is used for the illumination light on the basis of the presence or absence of input of the observation mode specification signal, and the type of the observation mode specified by the observation mode specification signal (S312). The specific illumination light is illumination light in an observation mode in which a doctor or the like often desires to execute the discrimination processing. In a case where the illumination light is switched to the specific illumination light (S312: YES), the discrimination processing control unit 383 executes the discrimination processing in the discrimination processing unit 82 (S313). In a case where the discrimination processing is not being executed in the immediately preceding frame, this substantially becomes a start of the discrimination processing. On the other hand, in a case where the illumination light is switched to illumination light other than the specific illumination light (S312: NO), the discrimination processing control unit 383 skips the discrimination in the discrimination processing unit 82. In a case where the discrimination processing is being executed in the immediately preceding frame, this substantially becomes an end of the discrimination processing.

By repeating the above operation till the end of the observation (S314), the discrimination processing is automatically performed while the observation mode is an observation mode in which the specific illumination light is used, and the discrimination processing also automatically ends in an interlocking manner in a case where the observation mode is switched to other observation modes in which the specific illumination light is not used. In this way, the score 99 that is the discrimination result can be provided by starting the discrimination processing in a case where there is switching to "an observation mode in which the specific illumination light is used" in many cases which a doctor or the like desires combined use of the discrimination processing, and performing the discrimination processing at an appropriate timing when a doctor or the like probably desires the discrimination processing in a case where the discrimination processing is ended in a case where there is switching to observation modes in which other illumination light is used. Then, the processing load on the processor device 16 can be suppressed without vainly performing the discrimination processing at unnecessary timings.

In the above third embodiment, the discrimination processing control unit 383 starts or ends the discrimination processing on the basis of the observation mode specification signal. However, the discrimination processing control unit 383 can detect the switching of the illumination light and the observation modes, using the endoscope image instead of the observation mode specification signal. In this case, the discrimination processing control unit 383 acquires the endoscope image from the image acquisition unit 54 or the image generation unit 81. Then, the switching of the illumination light and the observation modes is detected on the basis of the feature (color scheme or the like) of the acquired endoscope image.

In addition, the specific illumination light is, for example, illumination light with a wavelength of 450 nm or less. That is, in a case where the illumination light is switched to the illumination light with a wavelength of 450 nm or less, it is preferable to start the discrimination processing. In a case where the illumination light with a wavelength of 450 nm or less is used, it is easy to observe fine structures, such as blood vessels or pit patterns of the mucous membrane surface layer. Thus, in a case where the illumination light with a wavelength of 450 nm or less, a doctor or the like often desires detailed observation and discrimination results for diagnosis or the like. The "using the illumination light with a wavelength of 450 nm or less" means that the illumination light with a wavelength of 450 nm or less is substantially independently used and the observation target is imaged only with reflected light or the like of the illumination light with a wavelength of 450 nm or less.

Fourth Embodiment

The endoscope system 10 can start or end the discrimination processing on the basis of "the change in the operation of the endoscope 12 or the endoscope image" different from the above first embodiment, second embodiment, and third embodiment. For example, the discrimination processing can be started in a case where an object has passed through a channel inserted into the endoscope 12. The channel inserted into the endoscope 12 is, for example, a forceps channel 401 for allowing treatment tools, such as forceps, to be inserted therethrough and protruded toward the observation target from the distal end part 12d, and an air/water supply channel 402 for allowing water, air, or the like to pass therethrough to allow water, air, or the like to be jetted toward the observation target from the distal end part 12d (refer to FIG. 11).

Figure 11:
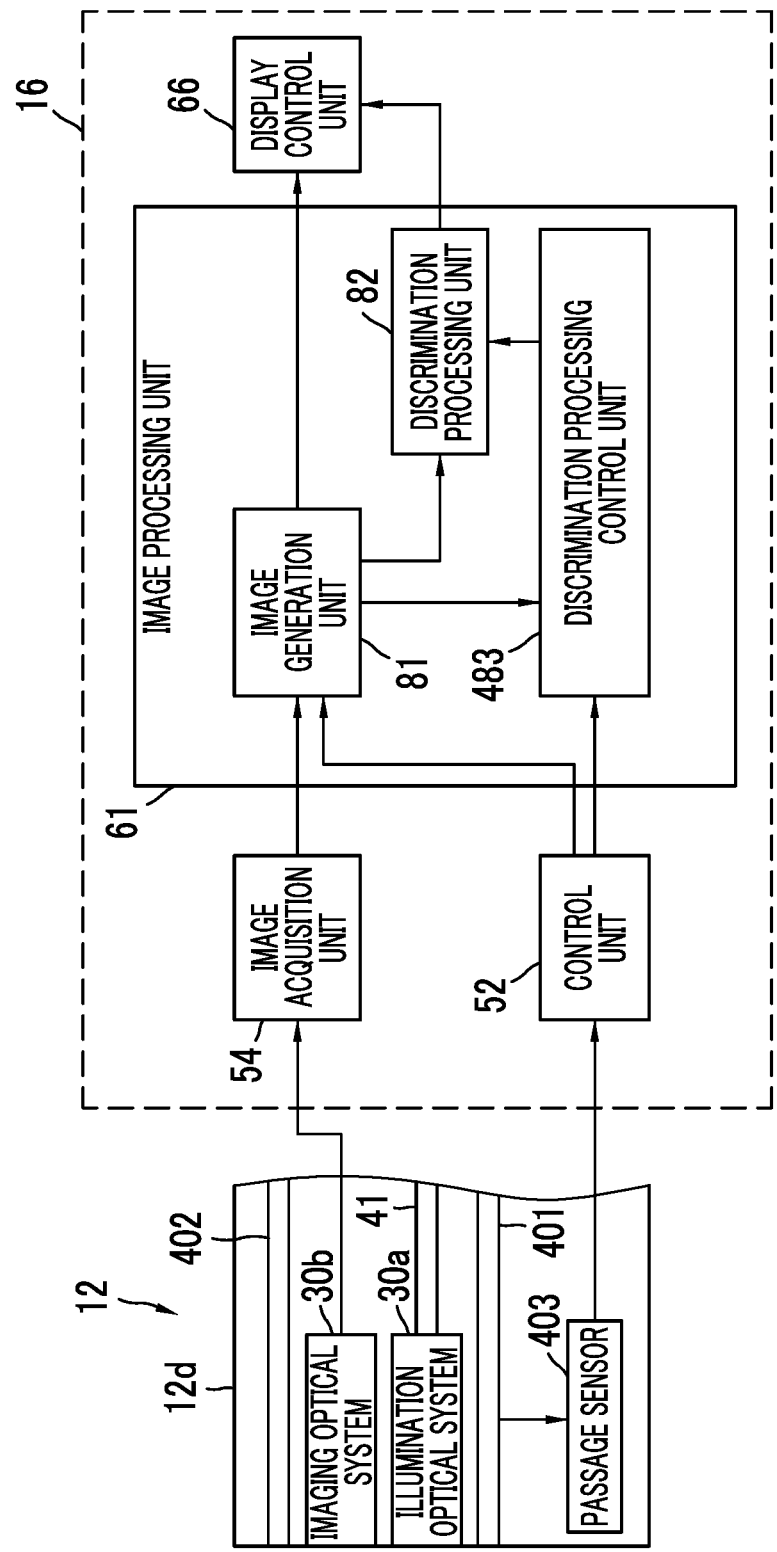
FIG. 11 is a block diagram of an image processing unit and the like in a fourth embodiment.

In a case where the object has passed the channel inserted into the endoscope 12 and the discrimination processing is started or ended, as illustrated in FIG. 11, a passage sensor 403 that detects passage of treatment tools, such as forceps, is provided in the middle of the forceps channel 401 (for example, near the distal end part 12d). Additionally, the image processing unit 61 is provided with a discrimination processing control unit 483 instead of the discrimination processing control unit 83 and the like of the first embodiment. The discrimination processing control unit 483 acquires a detection signal of a treatment tool from the passage sensor 403 via the control unit 52. Then, the discrimination processing is started or ended in a case where it is detected that a distal end or the like of the treatment tool has passed through the forceps channel 401.

Figure 12:
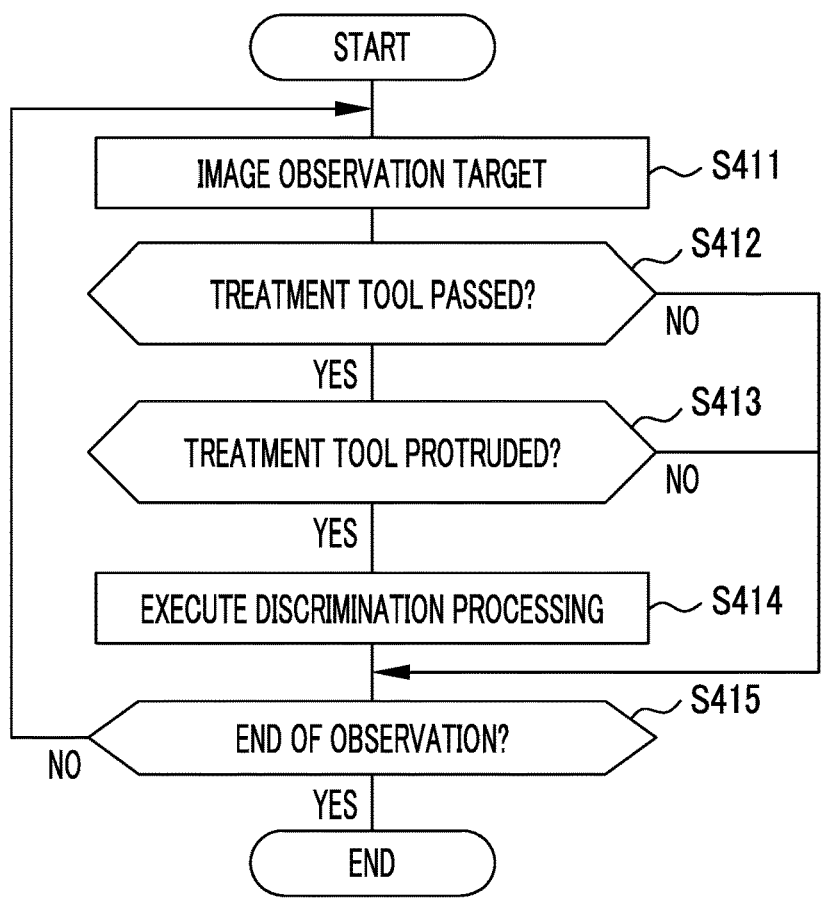
FIG. 12 is a flowchart illustrating a flow of start and end of discrimination processing in the fourth embodiment.

Specifically, as illustrated in FIG. 12, in a case where the observation target is imaged (S411) and an endoscope image is acquired, the discrimination processing control unit 483 acquires the detection signal from the passage sensor 403, and detects whether or not the treatment tool has passed through the forceps channel 401 on the basis of the acquired detection signal (S412). Then, the discrimination processing is skipped in a case where the treatment tool has not passed through the forceps channel 401 (S412: NO). Additionally, in a case where the passage of the treatment tool through the forceps channel 401 is detected from a state in which the treatment tool is not inserted through the forceps channel 401 (S412: YES), and the treatment tool is protruded toward the observation target from the distal end part 12d, (S413: YES), the discrimination processing control unit 483 execute the discrimination processing in the discrimination processing unit 82 (S414). In a case where the discrimination processing is not being executed in the immediately preceding frame, this substantially becomes a start of the discrimination processing. On the other hand, even in a case where the treatment tool has passed through the forceps channel 401, (S412: YES), a case where the passage of the treatment tool is again detected is a case where the treatment tool is retracted after the passage of the treatment tool is detected (S413: NO). Thus, the discrimination processing control unit 483 skips the discrimination processing in the discrimination processing unit 82. In a case where the discrimination processing is being executed in the immediately preceding frame, this substantially becomes an end of the discrimination processing.

By repeating the above operation till the end of the observation (S415), the discrimination processing is automatically performed only in a case where the treatment tool is protruded from the distal end part 12d, and the discrimination processing is automatically ended in a case where the treatment tool is retracted. Additionally, the discrimination processing is not performed in a case where the treatment tool is not being used at all. Since the treatment tool is used in a case where a lesion or the like is present and the treatment therefor is necessary, it is often desirable to perform the discrimination processing. For this reason, in a case where the discrimination processing is performed at the time of the use of the treatment tool as described above, the discrimination processing can be performed at an appropriate timing when a doctor or the like performs the discrimination processing, and the score 99 that is the discrimination result can be automatically provided. Additionally, the processing load on the processor device 16 can be suppressed without vainly performing the discrimination processing at unnecessary timings.

Figure 13:
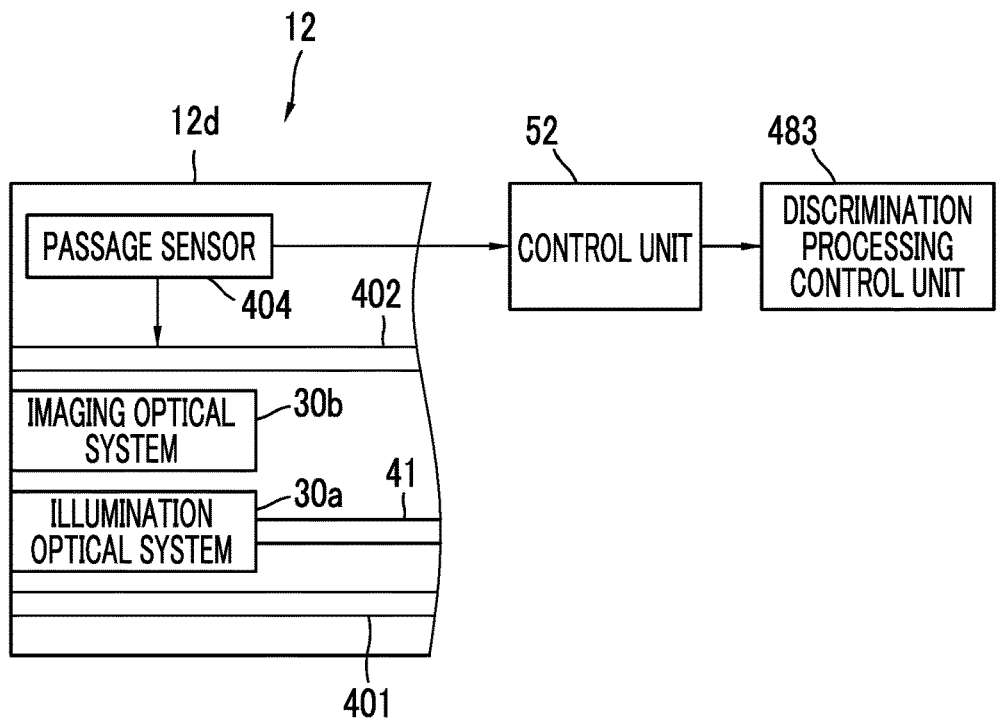
FIG. 13 is an explanatory view of a modification example.

In the above third embodiment, the forceps channel 401 is provided with the passage sensor 403, and the passage of the treatment tool is detected. Instead of this, however, passage of water in the air/water supply channel 402 may be detected. In this case, as illustrated in FIG. 13, the passage sensor 404 that detects passage of water or the like is provided in the middle of the air/water supply channel 402 (for example, near the distal end part 12d). Then, the discrimination processing control unit 483 starts the discrimination processing in a case where the water or the like has passed through the air/water supply channel 402. Since the water or the like is jetted, for example, a case where a portion to which the water or the like is applied or a peripheral portion thereof is observed in more detail, there is a case where it is desirable to simultaneously perform the discrimination processing. For this reason, as described above, in a case where jetting of the water or the like is detected and the discrimination processing is performed in a case where the jetting of the water or the like is detected, the discrimination processing can be performed at an appropriate timing when a doctor or the like desires the discrimination processing, and the score 99 that is the discrimination result can be automatically provided. Additionally, the processing load on the processor device 16 can be suppressed without vainly performing the discrimination processing at unnecessary timings.

In addition, it is preferable that the object that to be detected by the passage sensor 404 in the air/water supply channel 402 is water, or a coloring agent that stains water or the structure or the like of the observation target. This is because the coloring agent is used to make it easy to observe the structure or the like of the observation target, and thus, the time of spraying of the coloring agent is also the timing when a doctor or the like desires the discrimination processing.

Additionally, as described above, in a case where the water or the coloring agent has passed through the air/water supply channel 402, it is preferable to end the discrimination processing in a case where the discrimination processing is started or after a certain preset time has elapsed after the start of the discrimination processing. This is because the time for the water or the coloring agent to pass through the air/water supply channel 402 is extremely slight and a little time after the water or the coloring agent is jetted from the distal end part 12d is the time for obtaining the effect that the water or the coloring agent is jetted and observing the observation target.

In the above fourth embodiment and modification example, the passage sensor 403 or the passage sensor 404 is used. However, the discrimination processing control unit 483 can detect the water or the coloring agent by using the endoscope image instead of using the passage sensor 403 or the passage sensor 404. In this case, the discrimination processing control unit 483 acquires the endoscope image from the image acquisition unit 54 or the image generation unit 81. Then, the jetting of the water, the coloring agent, or the like is detected on the basis of a change (disappearance of residue or the like, a change in the color of the observation target resulting from the coloring agent, or the like) in the feature of the acquired endoscope image.

Fifth Embodiment

The endoscope system 10 can start or end the discrimination processing on the basis of "the change in the operation of the endoscope 12 or the endoscope image" different from the above first embodiment, second embodiment, the third embodiment, and fourth embodiment. For example, the discrimination processing can be started or ended in a case where a position where the endoscope 12 images the observation target has changed or in a case where the position where the endoscope 12 images the observation target does not change. Here, the change in the imaging position includes the change in the imaging position resulting from the change of the orientation of the distal end part 12d with respect to the observation target in addition to a change in the imaging position resulting from the insertion and removal of the insertion part 12a.

Figure 14:
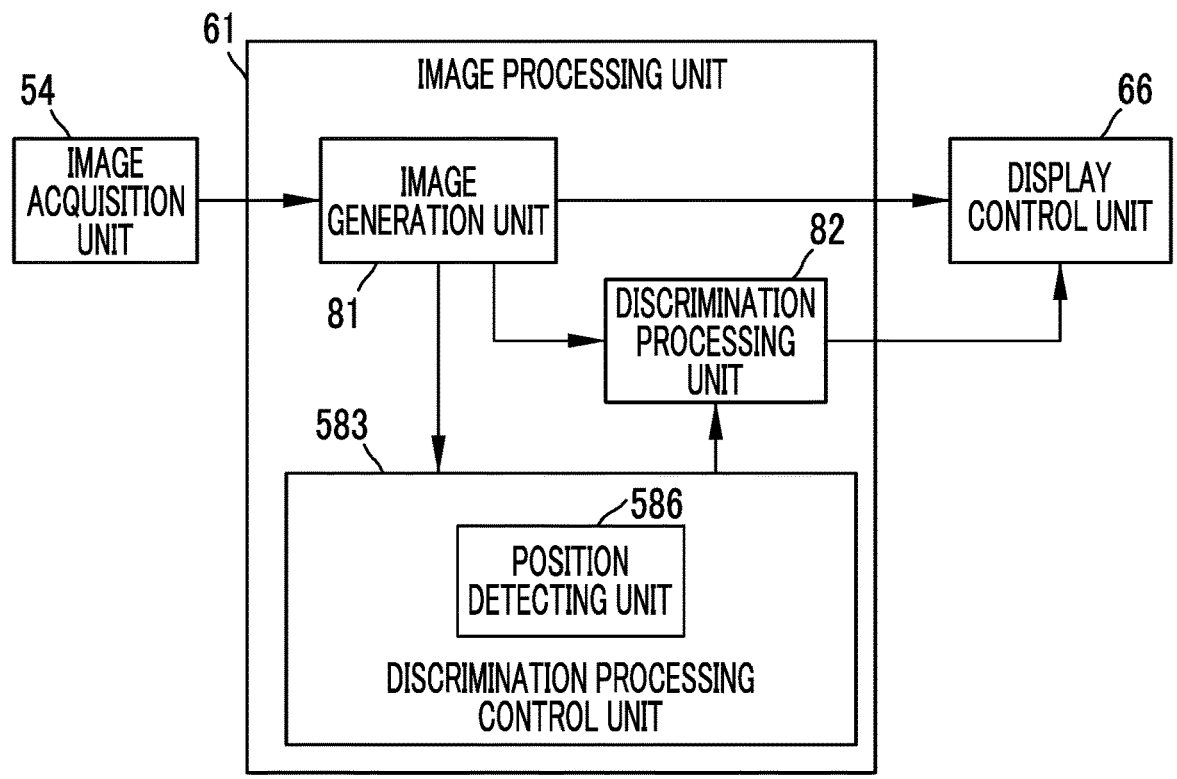
FIG. 14 is a block diagram of an image processing unit in a fifth embodiment.

As described above, in a case where the position where the endoscope 12 images the observation target has changed or in a case where the position where the endoscope 12 images the observation target does not change, and in a case where the discrimination processing is started or ended, as illustrated in FIG. 14, the image processing unit 61 is provided with a discrimination processing control unit 583 instead of the discrimination processing control unit 83 and the like of the first embodiment. The discrimination processing control unit 583 comprises the position detecting unit 586. The position detecting unit 586 detects the change or non-change of the position (hereinafter referred to as an imaging position) where the endoscope 12 images the observation target, using the endoscope image. For example, the position detecting unit 586 acquires the endoscope image from the image acquisition unit 54 or the image generation unit 81, and stores the above endoscope images of at least one past frame or more. Then, in a case where an endoscope image is newly acquired, the change in the imaging position is detected on the basis of the change of the observation target reflected on the endoscope image, by comparing the newly acquired endoscope image with the stored past endoscope images.

The discrimination processing control unit 583 detects the change in the imaging position on the basis of the change of the observation target reflected on the endoscope image by using the detection result of the position detecting unit 586. Then, the discrimination processing control unit 583 controls the start and end of the discrimination processing in the discrimination processing unit 82 on the basis of the detected change or non-change in the imaging position. In the present embodiment, the discrimination processing control unit 583 starts the discrimination processing in a case where the imaging position has changed, and ends the discrimination processing in a case where the imaging position does not change.

Figure 15:
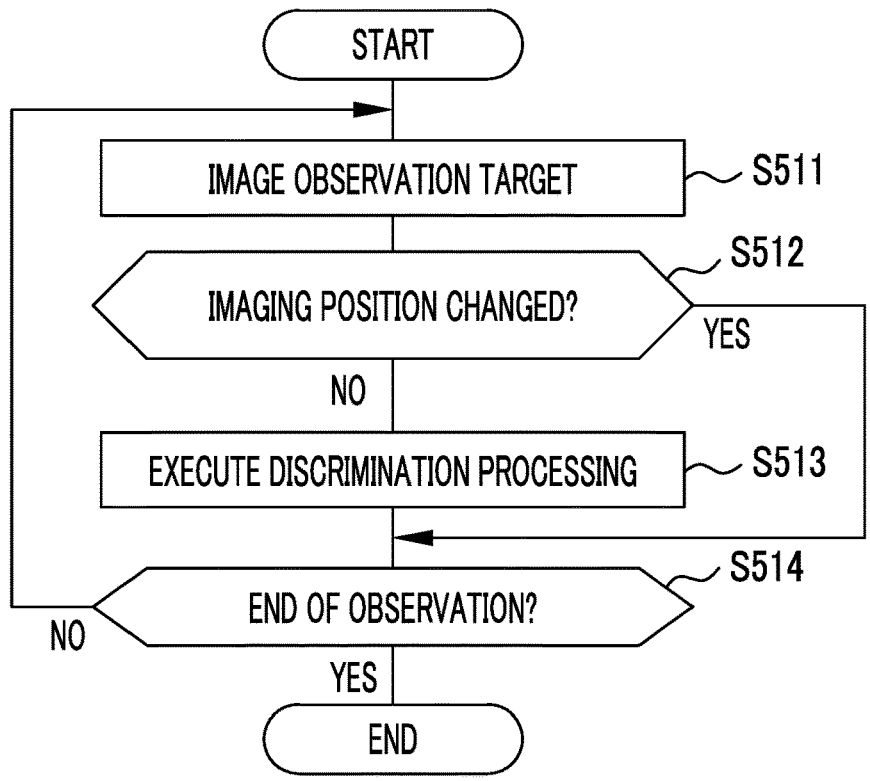
FIG. 15 is a flowchart illustrating a flow of start and end of discrimination processing in the fifth embodiment.

Specifically, as illustrated in FIG. 15, in a case where the observation target is imaged (S511) and the discrimination processing control unit 583 and the position detecting unit 586 acquire the endoscope image, the position detecting unit 586 compares the stored past endoscope images with the newly acquired endoscope image, and detects the change in the imaging position. in a case where the imaging position does not change or in a case where the change in the imaging position has stopped (S512: NO), the discrimination processing control unit 583 executes the discrimination processing in the discrimination processing unit 82 (S513). In a case where the discrimination processing is not being executed in the immediately preceding frame, this substantially becomes a start of the discrimination processing. On the other hand, in a case where there is a change in the imaging position (S512: YES), the discrimination processing control unit 583 skips the discrimination processing in the discrimination processing unit 82. In a case where the discrimination processing is being executed in the immediately preceding frame, this substantially becomes an end of the discrimination processing.

By repeating the above operation till the end of the observation (S514), the discrimination processing is automatically performed in a case where there is no change in the imaging position, and the discrimination processing is also automatically ended in an interlocking manner in a case where the imaging position changed. In this way, the discrimination processing is performed in a case where there is no change in the imaging position. This is because the case where there is no change in the imaging position is a case where it is necessary to observe in detail whether or not the observation target at the imaging position has a lesion in detail, and it is desirable to simultaneously perform the discrimination processing. Hence, in a case where the discrimination processing is started and ended on the basis of the change in the imaging position as described above, the discrimination processing can be performed at an appropriate timing when a doctor or the like desires the discrimination processing, and the score 99 that is the discrimination result can be provided. Then, the processing load on the processor device 16 can be suppressed without vainly performing the discrimination processing at unnecessary timings.

In the above fifth embodiment, in a case where there is no change in the imaging position, the discrimination processing is performed. Change, however, the discrimination processing may be is started in a case where there is a change in the imaging position, and the discrimination processing may be ended in a case where there is no change in the imaging position. In this way, in a case where the specific contents of the discrimination processing are mainly useful for search (so-called screening) of the presence or absence of a lesion or the like, the screening can be supported by performing the discrimination processing at the time of screening with a large change in the imaging position. Of course, in a case where both the discrimination processing suitable for detailed observation and the discrimination processing suitable for the time of the screening are performed, the discrimination processing suitable for the detailed observation can be performed in a case where there is no change in the imaging position, and the discrimination processing suitable for the time of the screening can be performed in a case where there is a change in the imaging position.

In addition, the "there is no change in the imaging position (no change in the imaging position)" means that the change in the imaging position is small and there is almost no change in the imaging position, as compared to at the time of the screening or the like. The "there is a change in the imaging position" means that the change in the imaging position is large, and the imaging position is not almost stationary, as compared to at the time of detailed observation.

Figure 16:
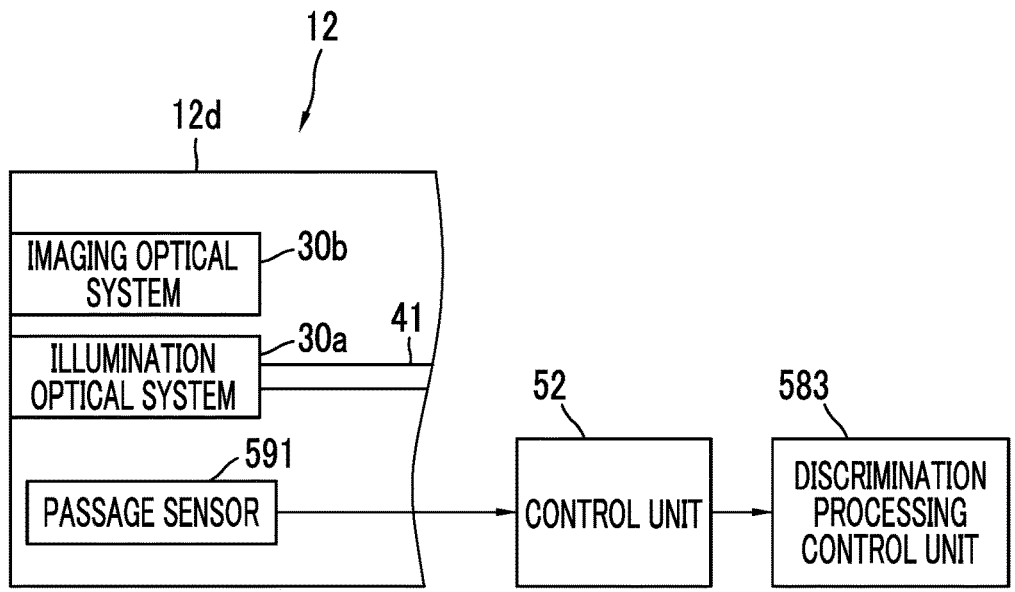
FIG. 16 is an explanatory view of a modification example.

In the above fifth embodiment and modification example, a discrimination processing control unit 583 detects the imaging position using the endoscope image. However, as illustrated in FIG. 16, the imaging position can be detected using a position sensor 591 (refer to FIG. 16) instead of using the endoscope image. The position sensor 591 is provided, for example, at the distal end part 12d of the endoscope 12, and detects the relative position of the distal end part 12d or the like with an examination table (not illustrated). Then, the discrimination processing control unit 583 detects a change (or no change) in the imaging position on the basis of a change (or no change) in the position of the distal end part 12d to be detected by the position sensor 591. The position sensor 591 may be a sensor that detects the insertion length of the insertion part 12a into the subject.

Sixth Embodiment

The endoscope system 10 can start or end the discrimination processing on the basis of the "change in the operation of the endoscope 12 or the endoscope image" different from the above first embodiment, second embodiment, third embodiment, fourth embodiment, and fifth embodiment. For example, the discrimination processing can be started or ended in a case where the endoscope 12 captures a still image of the observation target (that is, in a case where there is a change in the operation of an endoscope 12).

Figure 17:
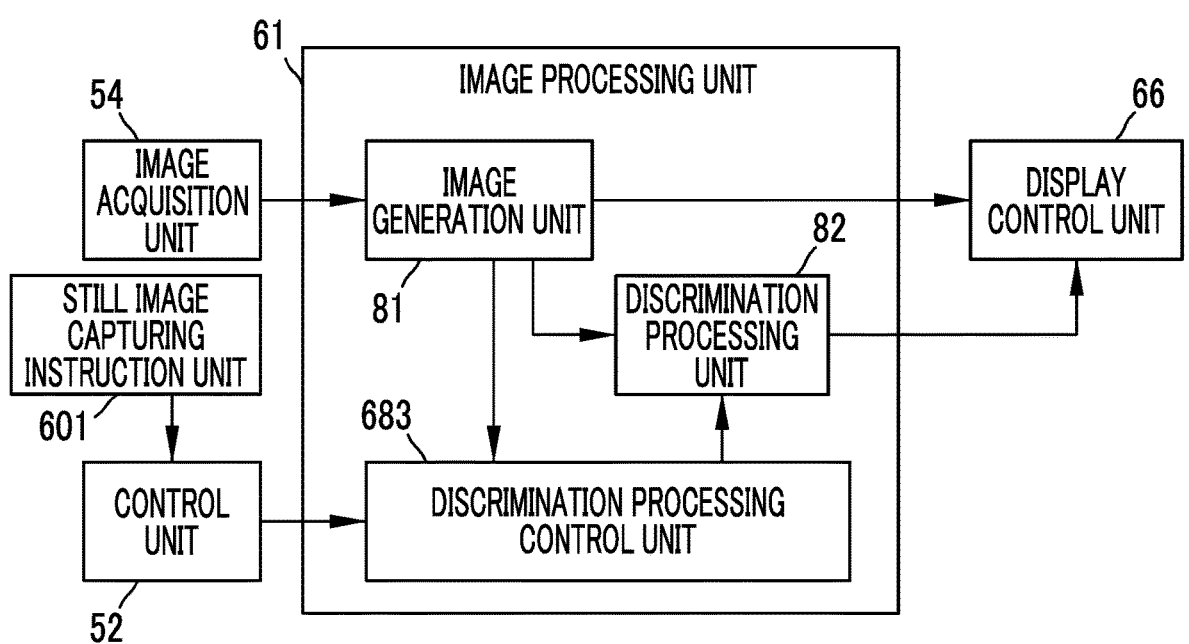
FIG. 17 is a block diagram of an image processing unit in a sixth embodiment.

As illustrated in FIG. 17, in a case where the endoscope 12 captures the still image of the observation target, a still image capturing instruction unit 601 that inputs a capturing instruction for the still image to the endoscope 12 is provided. The still image capturing instruction unit 601 is, for example, a so-called freeze button or so-called release button provided in the operating part 12b. In addition, a foot switch (not illustrated) or the like can be the still image capturing instruction unit 601. The still image capturing instruction unit 601 inputs the capturing instruction for the still image to the control unit 52. As a result, the control unit 52 images the observation target on still image capturing conditions, using the endoscope 12, and generates at least one still image of the observation target, using the image processing unit 61.

Additionally, the image processing unit 61 is provided with a discrimination processing control unit 683 instead of the discrimination processing control unit 83 and the like in the above respective embodiments. The discrimination processing control unit 683 acquires the capturing instruction for the still image from the still image capturing instruction unit 601 via the control unit 52. As a result, the discrimination processing control unit 683 detects that the endoscope 12 has captured the still image. The discrimination processing control unit 683 starts the discrimination processing in a case where the endoscope 12 has captured the still image.

Figure 18:
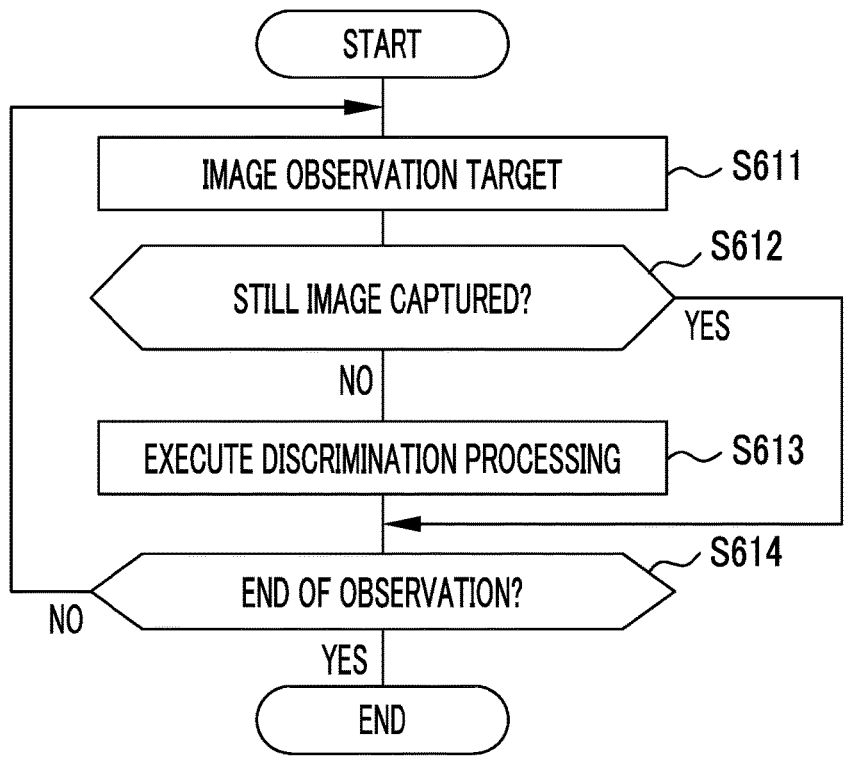
FIG. 18 is a flowchart illustrating a flow of start and end of discrimination processing in the sixth embodiment.

Specifically, as illustrated in FIG. 18, while the observation target is imaged for a moving image (S612: YES), the discrimination processing control unit 683 executes the discrimination processing (S613) in a case where and the endoscope 12 has captured the still image of the observation target (S611). In a case where the discrimination processing is not being executed in the immediately preceding frame, this substantially becomes a start of the discrimination processing. On the other hand, in a case where the endoscope 12 does not capture a still image (S612: NO), the discrimination processing control unit 683 skips the discrimination processing (S613). For this reason, in the immediately preceding frame, in a case where the still image is captured and the discrimination processing is being executed, this substantially becomes an end of the discrimination processing.

By repeating the above operation till the end of the observation (S614), the discrimination processing is automatically performed in a case where the endoscope 12 captures the still image of the observation target, and the discrimination processing is not performed in a case where the endoscope 12 does not capture the still image of the observation target. The endoscope 12 captures the still image of the observation target in a case where the detailed observation, such as a lesion or the like being in the observation target, is required. Hence, in a case where the discrimination processing is started and ended in a case where the endoscope 12 captures the still image as described above hence, the discrimination processing can be performed at an appropriate timing when a doctor or the like desires the discrimination processing, and the score 99 that is the discrimination result can be provided. Then, the processing load on the processor device 16 can be suppressed without vainly performing the discrimination processing at unnecessary timings.

In addition, the respective discrimination processing control units, such as the discrimination processing control unit 83 and the like in the above first embodiment, second embodiment, third embodiment, fourth embodiment, and fifth embodiment controls the start and end of the discrimination processing in the discrimination processing unit 82 on the basis of the change in the operation of the endoscope 12 or the endoscope image. However, the respective discrimination processing control units of the above respective embodiments can control only any one of the start or the end of the discrimination processing in the discrimination processing unit 82 on the basis of the change in the operation of the endoscope 12 or the endoscope image.

Additionally, in a case Where the respective discrimination processing control units in the above first embodiment, second embodiment, third embodiment, fourth embodiment, and fifth embodiment start the discrimination processing on the basis of the change in the operation of the endoscope 12 or the endoscope image, the discrimination processing can be ended after the start of the discrimination processing or in a case where a certain preset time has elapsed. In this way, in a case where the discrimination processing is ended in a case where a certain preset time has elapsed after the start of the discrimination processing, it is not necessary to detect the change in the operation of the endoscope 12 or the change of the endoscope image for the end of the discrimination processing. Therefore, the processing of the respective discrimination processing control units can be reduced.

Seventh Embodiment

Figure 19:
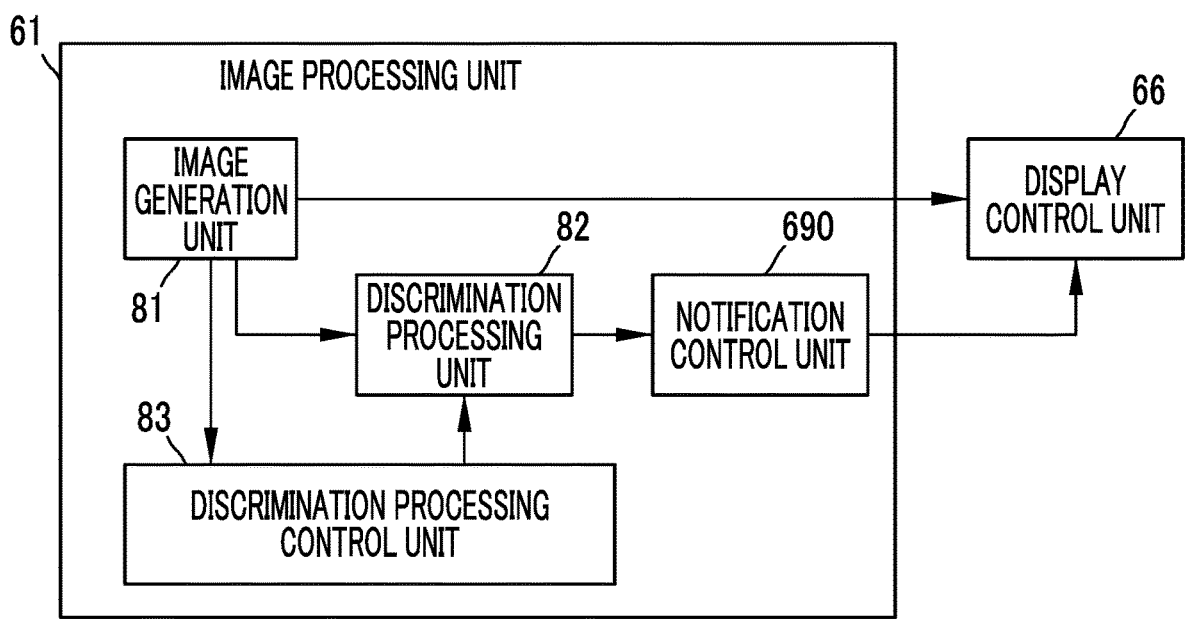
FIG. 19 is a block diagram of an image processing unit in seventh embodiment.

In the above first embodiment, second embodiment, third embodiment, fourth embodiment, fifth embodiment, and sixth embodiment, the start or the end of the discrimination processing is controlled on the basis of the change in the operation of the endoscope 12 or the endoscope image. However, notification of the discrimination result can be started or ended on the basis of the change in the operation of the endoscope 12 and the endoscope image. In this case, as illustrated in FIG. 19, the image processing unit 61 is provided with a notification control unit 690 in addition to the discrimination processing control unit 83 and the like in the first embodiment.

The notification control unit 690 acquires the discrimination result from the discrimination processing unit 82. Then, the notification control unit 690 inputs the acquired discrimination result to the display control unit 66 or inputs the acquired discrimination result to other output devices (for example, a loudspeaker that outputs sound or voice or an indicator that emits light or the like). As a result, the notification control unit 690 notifies a user of the discrimination result, for example, using any of voice, an image, or a message, or using a combination thereof.

Additionally, the notification control unit 690 always does not output the acquired discrimination result to a display control unit 66 or the like, but determines whether or not the acquired discrimination result is outputs to the display control unit 66 or the like on the basis of the change in the operation of the endoscope 12 or the endoscope image similarly to any of the respective discrimination processing control units in the above respective embodiments. As a result, the notification control unit 690 starts or ends the notification of a discrimination result on the basis of the change in the operation of the endoscope 12 or the endoscope image, For example, in a case where the score 99 is acquired as the determination result and it is determined that it is appropriate to provides the notification of the discrimination result on the basis of the change in the operation of the endoscope 12 or the endoscope image, the notification control unit 690 provides a notification of the discrimination result by inputting he acquired score 99 to the display control unit 66 and consequently displaying the score 99 on the monitor 18 as a result (refer to FIG. 5).

In addition, the notification control unit 690 can control the start or the end of the notification of the discrimination result on the basis of the change in the operation of the endoscope 12 or the endoscope image for every discrimination result in a case where a plurality of discrimination results are acquired. In addition, the notification control unit 690 can start or end the notification of the discrimination result with the same reference as a reference for the start or the end of the discrimination processing. Additionally, the notification control unit 690 can also set a reference for starting or ending the notification of the discrimination result to a reference different from the start or the end of the discrimination processing. For example, in a case where the discrimination processing control unit 83 controls the start or the end of the discrimination processing by the method of the first embodiment, the notification control unit 690 can start or end the notification of the discrimination result with the same reference as the discrimination processing control unit 283 of the second embodiment.

The notification control unit 690 can provide a notification of the determination result and information relevant to the determination result together. For example, as illustrated in FIG. 20, the notification control unit 690 provides a notification of a profile 691 of the specific portion (lesion), an image 694 of the similar case, or a message 693, such as "this region has the possibility of cancer", as the information relevant to the determination result in addition to the score 692 and invasiveness 695 of a lesion that are examples of the determination result.

As the profile 691 of the specific portion (lesion), for example, the positional information of the specific portion within the endoscope image subjected to the discrimination processing can be known from the discrimination processing unit 82. The message 693 can be obtained by collating the determination result with a message database (not illustrated) that is prepared in advance. In FIG. 20, although a notification is provided by displaying the message 693 on the monitor 18, a notification of the message 693 may be provided with voice. The image 694 of the similar case is acquirable from the case database (not illustrated) in conformity with the discrimination result. Although one image 694 of the similar case is displayed In FIG. 20, a plurality of images of the similar case can be displayed on the monitor 18 in a case where there are the plurality of images 694 of the similar case.

Figure 20:
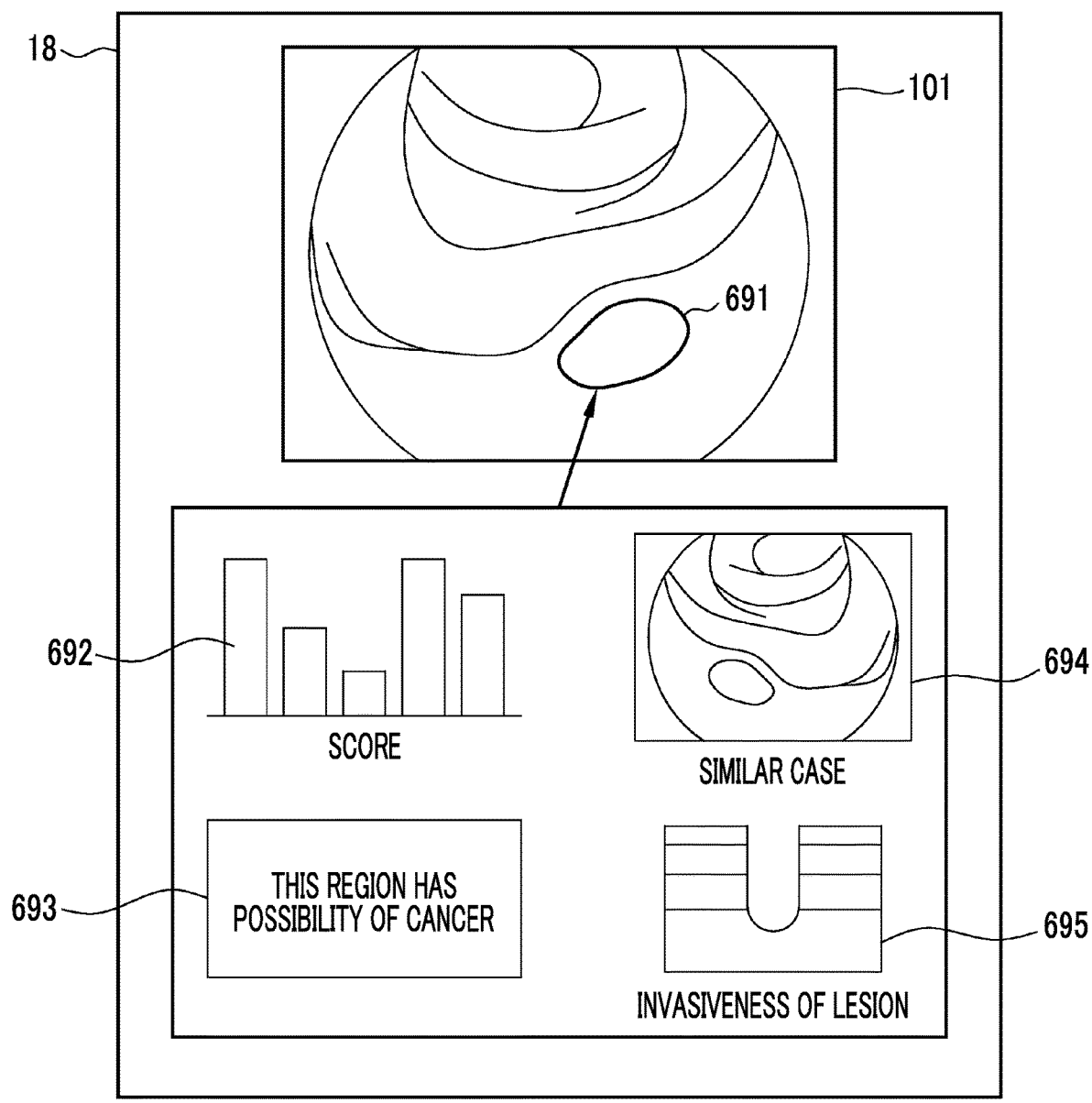
FIG. 20 is an example of display of a monitor in seventh embodiment.
Figure 21:
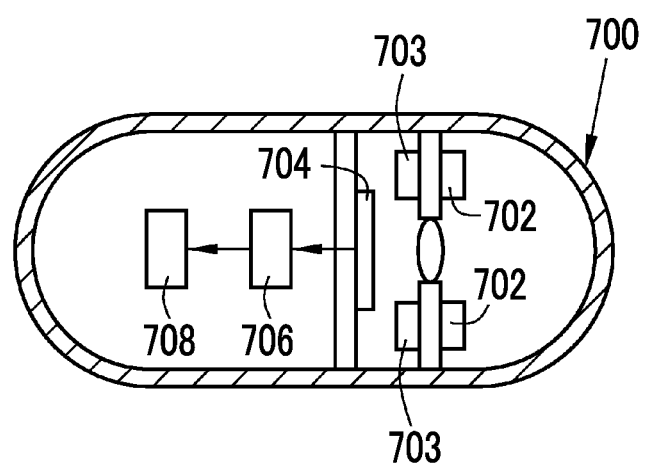
FIG. 21 is a schematic view of a capsule endoscope.

In addition, in FIG. 20, a plurality of types of scores 692 are displayed in the form of graphs. However, the same display can be performed also in the above respective embodiment, such as the first embodiment. Additionally, in FIG. 20, the invasiveness 695 of the lesion that is an example of the determination result is illustrated in the monitor 18. However, in a case where the determination result is displayed in the form of drawings, tables, or others the determination result can be expressed also in the form of drawings, tables, or others in the above respective embodiments, such as the first embodiment. The same applies to determination results other than the score 692 and the invasiveness 695 of the lesion. The profile 691 of the lesion, the message 693, and the image 694 of the similar case are examples of the information relevant to the determination result, and the notification control unit 690 can provide a notification of information relevant to the other determination results. For example, the notification control unit 690 provides a notification of the position of the specific portion within the subject, or the endoscope image (past image) captured in the past diagnosis as the information relevant to the determination results, in addition to the above.

In addition, in the seventh embodiment, the image processing unit 61 can comprise each discrimination processing control unit of each embodiment, such as the discrimination processing control unit 83, in the first embodiment, and the notification control unit 690. However, the image processing unit 61 can comprise only the notification control unit 690 instead of the discrimination processing control unit 83 and the like. In this case, the endoscope system 10 comprises the image acquisition unit 54 that acquires the endoscope image obtained by imaging the observation target using the endoscope, the discrimination processing unit 82 that discriminates a portion having the specific feature in the observation target by performing the discrimination processing using the endoscope image, and the notification control unit 690 that controls the start or the end of the notification of the discrimination result that is a result of the discrimination processing on the basis of the change in the operation of the endoscope 12 or the endoscope image.

In addition, either in a case where the image processing unit 61 comprises the notification control unit 690 together with the discrimination processing control unit 83 and the like or in a case where the image processing unit 61 comprises only the notification control unit 690 instead of the discrimination processing control unit 83 and the like, the notification control unit 690 can be configured similarly to the discrimination processing control unit 83 and the like of the first embodiment.

For example, it is preferable that the notification control unit 690 comprises the feature amount calculation unit 86 that calculates the feature amount using the endoscope image, and the comparison unit 87 that compares the feature amount with the threshold value, and the notification control unit 690 starts or ends the notification of the discrimination result on the basis of the comparison result in the comparison unit 87.

Additionally, the notification control unit 690 can start or end the notification of the discrimination result in a case where the endoscope 12 has enlarged or reduced the observation target.

The notification control unit 690 can start the notification of the discrimination result in a case where the illumination light to be used in a case where the endoscope 12 images the observation target is switched to the specific illumination light, and can end the notification of the discrimination result in a case where the illumination light to be used in a case where the endoscope images the observation target is switched to the illumination light other than the specific illumination light.

The notification control unit 690 can start the notification of the discrimination result in a case where the illumination light is switched to the illumination light with a wavelength of 450 nm or less.

The notification control unit 690 can start or end the notification of the discrimination result in a case where the object has passed through the channel inserted through the endoscope 12.

The notification control unit 690 can start the notification of the discrimination result in a case where the water has passed the channel.

The notification control unit 690 can start the notification of the discrimination result in a case where the coloring agent has passed the channel.

The notification control unit 690 can start or end the notification of the discrimination result in a case where the position where an endoscope images the observation target has changed or in a case where the position where the endoscope images the observation target does not change.

The notification control unit 690 can detect the position where the endoscope images the observation target on the basis of the change of the observation target reflected on the endoscope image.

The notification control unit 690 can detect the position where the endoscope images the observation target, using the position sensor.

The notification control unit 690 can end the notification of the discrimination result in a case where the position where the endoscope 12 images the observation target has changed.

The notification control unit 690 can start the notification of the discrimination result on the basis of the change in the operation of the endoscope 12 or the endoscope image, and can end the notification of the discrimination result after a certain preset time has elapsed after the notification start of the discrimination result.

The notification control unit 690 can start or end the notification of the discrimination result in a case where the endoscope 12 has captured the still image.

In the above respective embodiments, the invention is carried out in the endoscope system 10 that performs observation by inserting the endoscope 12 provided with the image sensor 48 into the subject. However, the invention is also suitable in a capsule endoscope system. As illustrated in FIG. 17, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 functions similarly to the light source control unit 22 and the control unit 52. Additionally, the control unit 703 is capable of wirelessly communicating with the processor device of the capsule endoscope system, using the transmission/reception antenna 708. Although the processor device of the capsule endoscope system is substantially the same as that of the processor device 16 of the above embodiment, an image processing unit 706 corresponding to the image acquisition unit 54 and the image processing unit 61 is provided in the capsule endoscope 700, and the endoscope image is transmitted to the processor device via the transmission/reception antenna 708. The image sensor 704 is configured similarly to the image sensor 48.

10: endoscope system
12: endoscope
12*a*: insertion part
12*b*: operating part
12*c*: bending part
12*d*: distal end part
12*e*: angle knob
13*a*: zoom operating part
13*b*: mode changeover switch
14: light source device
16: processor device
18: monitor
19: console
20: light source unit
22: light source control unit
30*a* illumination optical system
30*b*: imaging optical system
41: light guide
45: illumination lens
46: objective lens
47: zoom lens
48: image sensor
52: control unit
54: image acquisition unit
56: DSP(Digital Signal Processor)
58: noise reduction unit
59: conversion unit
61: image processing unit
66: display control unit
71: CNN (Convolution Neural Network)
72: storage unit
81: image generation unit
82: discrimination processing unit
83, 283, 383, 483, 583, 683: discrimination processing control unit
86: feature amount calculation unit
87: comparison unit
99, 692: score
101, 102: endoscope image
401: forceps channel
402: air/water supply channel
403, 404: passage sensor
586: position detecting unit
591: position sensor
601: still image capturing instruction unit
690: notification control unit
691: profile
693: message
694: similar case image
695: lesion invasiveness
700: capsule endoscope
702: light source unit
703: control unit
704: image sensor
706: image processing unit
708: transmission/reception antenna

What is claimed is:

1. An endoscope system comprising:
a processor configured to:
    acquire an endoscope image obtained by imaging an observation target using an illumination light using an endoscope;
    discriminate a portion having a specific feature in the observation target by performing discrimination processing using the endoscope image; and
    control a start or an end of the discrimination processing on the basis of a change in operation of the endoscope or the endoscope image,
    wherein the processor is further configured to start the discrimination processing in a case where the illumination light is switched to specific illumination light, and end the discrimination processing in a case where the specific illumination light is switched to an illumination light other than the specific illumination light.

2. The endoscope system according to claim 1,
wherein the processor is further configured to:
    calculate a feature amount using the endoscope image, and
    compare the feature amount with a threshold value, and wherein the processor is further configured to start or end the discrimination processing on the basis of a comparison result.

3. The endoscope system according to claim 1, wherein the processor is further configured to start or end the discrimination processing in a case where the endoscope has enlarged or reduced the observation target.

4. The endoscope system according to claim 1, wherein the processor is further configured to start the discrimination processing in a case where the illumination light is switched to illumination light with a wavelength of 450 nm or less.

5. The endoscope system according to claim 1, wherein the processor is further configured to start or end the discrimination processing in a case where an object has passed through a channel inserted through the endoscope.

6. The endoscope system according to claim 5, wherein the processor is further configured to start the discrimination processing in a case where water has passed through the channel.

7. The endoscope system according to claim 5, wherein the processor is further configured to start the discrimination processing in a case where a coloring agent has passed through the channel.

8. The endoscope system according to claim 1, wherein the processor is further configured to start or end the discrimination processing in a case where a position where the endoscope images the observation target has changed or in a case where the position where the endoscope images the observation target does not change.

9. The endoscope system according to claim 8, wherein the processor is further configured to detect the position where the endoscope images the observation target on the basis of a change of the observation target reflected on the endoscope image.

10. The endoscope system according to claim 8, wherein the processor is further configured to detect the position where the endoscope images the observation target, using a position sensor.

11. The endoscope system according to claim 8, wherein the processor is further configured to end the discrimination processing in a case where the position where the endoscope images the observation target has changed.

12. The endoscope system according to claim 1, wherein the processor is further configured to start the discrimination processing on the basis of the change in the operation of the endoscope or the endoscope image, and end the discrimination processing after a certain preset time has elapsed after the start of the discrimination processing.

13. The endoscope system according to claim 1, wherein the processor is further configured to start or end the discrimination processing in a case where the endoscope has captured a still image.

14. The endoscope system according to claim 1, wherein the processor is further configured to:
a control a start or an end of notification of a discrimination result that is a result of the discrimination processing on the basis of the change in operation of the endoscope or the endoscope image, 15. The endoscope system according to claim 14, wherein the processor is further configured to:
calculate a feature amount using the endoscope image, and
compare the feature amount with a threshold value, and
wherein processor is further configured to start or end the notification of the discrimination result on the basis of a comparison result.

16. The endoscope system according to claim 14, wherein the processor is further configured to start or end the notification of the discrimination result in a case where the endoscope has enlarged or reduced the observation target.

17. The endoscope system according to claim 14, wherein the processor is further configured to start the notification of the discrimination result in a case where illumination light to be used in a case where the endoscope images the observation target is switched to specific illumination light, and end the notification of the discrimination result in a case where the illumination light to be used in a case where the endoscope images the observation target is switched to illumination light other than the specific illumination light.

18. The endoscope system according to claim 17, wherein the processor is further configured to start the notification of the discrimination result in a case where the illumination light is switched to illumination light with a wavelength of 450 nm or less.

19. The endoscope system according to claim 14, wherein the processor is further configured to start or end the notification of the discrimination result in a case where an object has passed through a channel inserted through the endoscope.

20. The endoscope system according to claim 19, wherein the processor is further configured to start the notification of the discrimination result in a case where water has passed the channel.

21. The endoscope system according to claim 19, wherein the processor is further configured to start the notification of the discrimination result in a case where a coloring agent has passed through the channel.

22. The endoscope system according to claim 14, wherein the processor is further configured to start or end the notification of the discrimination result in a case where a position where the endoscope images the observation target has changed or in a case where the position where the endoscope images the observation target does not change.

23. The endoscope system according to claim 22, wherein the processor is further configured to detect the position where the endoscope images the observation target on the basis of a change of the observation target reflected on the endoscope image.

24. The endoscope system according to claim 22, wherein the processor is further configured to detect the position where the endoscope images the observation target, using a position sensor.

25. The endoscope system according to claim 22, wherein the processor is further configured to end the notification of the discrimination result in a case where the position where the endoscope images the observation target has changed.

26. The endoscope system according to claim 14, wherein the processor is further configured to start the notification of the discrimination result on the basis of the change in the operation of the endoscope or the endoscope image, and end the notification of the discrimination result after a certain preset time has elapsed after the start of the notification of the discrimination result.

27. The endoscope system according to claim 14,
wherein the processor is further configured to start or end the notification of the discrimination result in a case where the endoscope has captured a still image.

28. The endoscope system according to claim 14,
wherein the processor is further configured to provide the notification of the discrimination result, using any of voice, an image, a message, or a combination thereof.

29. A processor device comprising:
a processor configured to:
   acquire an endoscope image obtained by imaging an observation target using an illumination light using an endoscope;
   discriminate a portion having a specific feature in the observation target by performing discrimination processing using the endoscope image; and
   control a start or an end of the discrimination processing on the basis of a change in operation of the endoscope or the endoscope image,
   wherein the processor is further configured to start the discrimination processing in a case where the illumination light is switched to specific illumination light, and end the discrimination processing in a case where the specific illumination light is switched to an illumination light other than the specific illumination light.

30. A method of operating an endoscope system comprising:
   a step of acquiring an endoscope image, which is obtained by imaging an observation target using an illumination light using an endoscope, using a processor;
   a step of discriminating a portion having a specific feature in the observation target by performing discrimination processing using the endoscope image, using the processor; and
   a step of controlling a start or an end of the discrimination processing on the basis of a change in operation of the endoscope or the endoscope image, using the processor,
   wherein the processor is configured to start the discrimination processing in a case where the illumination light is switched to specific illumination light, and end the discrimination processing in a case where the specific illumination light is switched to an illumination light other than the specific illumination light.

* * * * *